United States Patent [19]

Frick et al.

[11] Patent Number: 4,690,942
[45] Date of Patent: Sep. 1, 1987

[54] 1-ARYL-2-FLUORO-2-AZOLYL ALKANONES, ALKANOLS, ESTERS, AND ETHERS, COMPOSITION CONTAINING THEM, AND USE OF THEM TO CONTROL PHYTOPATHOGENIC MICROORGANISMS

[75] Inventors: Willy Frick, Pfeffingen; Alfred Meyer; Robert Nyfeler, both of Basel, all of Switzerland

[73] Assignee: CIBA-GEIGY Corporation, Ardsley, N.Y.

[21] Appl. No.: 681,989

[22] Filed: Dec. 14, 1984

[30] Foreign Application Priority Data

Dec. 20, 1983 [CH] Switzerland ............ 6757/83
Jun. 5, 1984 [CH] Switzerland ............ 2731/84

[51] Int. Cl.[4] ............ A01N 43/50; A01N 43/653; C07D 233/60; C07D 249/08
[52] U.S. Cl. ............ 514/383; 514/184; 514/189; 514/190; 514/191; 514/397; 514/399; 548/101; 548/262; 548/336; 548/341
[58] Field of Search ............ 548/262, 336, 341, 101; 514/383, 397, 399, 184, 189, 190, 191

[56] References Cited

U.S. PATENT DOCUMENTS

| | | | |
|---|---|---|---|
| 4,389,409 | 6/1983 | Miller | 514/399 |
| 4,406,909 | 9/1983 | Kramer et al. | 548/262 |
| 4,411,687 | 10/1983 | Zeeh et al. | 548/262 |
| 4,416,682 | 11/1983 | Worthington | 548/262 |
| 4,539,325 | 9/1985 | Heeres | 548/341 |
| 4,577,032 | 3/1986 | Fujita et al. | 548/341 |

FOREIGN PATENT DOCUMENTS

| | | | |
|---|---|---|---|
| 2431407 | 1/1976 | Fed. Rep. of Germany | 548/262 |
| 2937595 | 4/1981 | Fed. Rep. of Germany | 548/262 |

Primary Examiner—Henry R. Jiles
Assistant Examiner—Kurt G. Briscoe
Attorney, Agent, or Firm—Edward McC. Roberts; Meredith C. Findlay

[57] ABSTRACT

The invention relates to 1-aryl-2-fluoro-2-azolyl alkanones, alkanols, esters and ethers of formula 1

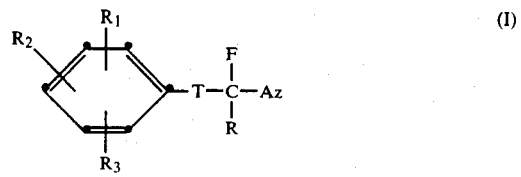

wherein
Az is 1H-1,2,4-triazole, 4H-1,2,4-triazole or 1H-imidazole;
T is —C(O)—, —CH(OH)— or one of the groups

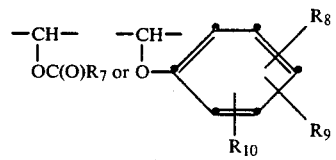

wherein
$R_7$ is $C_1$–$C_6$alkyl which is unsubstituted or substituted by $C_1$–$C_3$-alkoxy, halogen or cyano, or is $C_3$–$C_6$alkenyl, $C_3$–$C_6$alkynyl, $C_3$–$C_6$cycloalkyl, 2-furyl, 2-tetrahydrofuryl, or is phenyl or benzyl, each unsubstituted or substituted by halogen, nitro, $C_1$–$C_3$-alkyl, $C_1$–$C_3$alkoxy, $C_1$–$C_3$haloalkyl and/or $C_1$–$C_3$haloalkoxy;
$R_8$, $R_9$ and $R_{10}$ are each independently hydrogen, nitro, halogen, cyano, $C_1$–$C_3$alkyl, $C_1$–$C_3$alkoxy, $C_1$–$C_3$-haloalkoxy, —COO($C_1$–$C_3$alkyl), $NH_2$ or $NHCOCH_3$;
R is hydrogen or $C_1$–$C_6$alkyl;
$R_1$ and $R_2$ are each independently hydrogen, halogen, $C_1$–$C_6$alkyl, $C_1$–$C_6$-alkoxy, $C_1$–$C_6$haloalkyl, $C_1$–$C_6$-haloalkoxy, nitro and/or cyano; and
$R_3$ is hydrogen, halogen, $C_1$–$C_6$alkyl, $C_1$–$C_6$alkoxy, $C_1$–$C_6$haloalkyl, $C_1$–$C_6$ haloalkoxy, nitro, cyano and/or the group

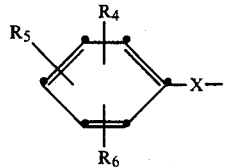

wherein
X is O, S, SO or $SO_2$;
$R_4$, $R_5$ and $R_6$ are each independently hydrogen, halogen, cyano, nitro, $C_1$–$C_6$alkyl, $C_1$–$C_6$alkoxy, $C_1$–$C_6$-haloalkyl and/or $C_1$–$C_6$haloalkoxy; and to the acid addition salts and metal complexes thereof.

These compounds have microbicidal properties and can be used in particular against diseases occurring in rice.

The invention also relates to the preparation and use of these compounds.

20 Claims, No Drawings

1-ARYL-2-FLUORO-2-AZOLYL ALKANONES, ALKANOLS, ESTERS, AND ETHERS, COMPOSITION CONTAINING THEM, AND USE OF THEM TO CONTROL PHYTOPATHOGENIC MICROORGANISMS

The present invention relates to novel substituted 1-aryl-2-fluoro-2-azolyl alkanones, alkanols, esters and ethers of the formula I below and to the acid addition salts and metal complexes thereof. The invention relates further to the preparation of these compounds and to microbicidal compositions which contain at least one of these compounds as active ingredient. The invention also relates to the preparation of said compositions and to the use of the novel compounds or compositions for controlling harmful microorganisms, preferably phytopathogenic fungi, in particular Piricularia species.

Accordingly, the invention relates to compounds of the general formula I

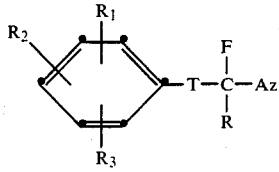

(I)

wherein

Az is 1H-1,2,4-triazole, 4H-1,2,4-triazole or 1H-imidazole;

T is —C(O)—, —CH(OH)— or one of the groups

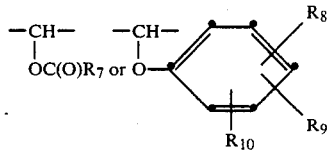

wherein $R_7$ is $C_1$–$C_6$alkyl which is unsubstituted or substituted by $C_1$–$C_3$alkoxy, halogen or cyano, or is $C_3$–$C_6$alkenyl, $C_3$–$C_6$alkynyl, $C_3$–$C_6$cycloalkyl, 2-furyl, 2-tetrahydrofuryl, or is phenyl or benzyl, each unsubstituted or substituted by halogen, nitro, $C_1$–$C_3$alkyl, $C_1$–$C_3$alkoxy, $C_1$–$C_3$haloalkyl and/or $C_1$–$C_3$haloalkoxy;

$R_8$, $R_9$ and $R_{10}$ are each independently hydrogen, nitro, halogen, cyano, $C_1$–$C_3$alkyl, $C_1$–$C_3$alkoxy, $C_1$–$C_3$haloalkoxy, —COO($C_1$–$C_3$alkyl), $NH_2$ or $NHCOCH_3$;

R is hydrogen or $C_1$–$C_6$alkyl;

$R_1$ and $R_2$ are each independently hydrogen, halogen, $C_1$–$C_6$alkyl, $C_1$–$C_6$alkoxy, $C_1$–$C_6$haloalkyl, $C_1$–$C_6$haloalkoxy, nitro and/or cyano; and $R_3$ is hydrogen, halogen, $C_1$–$C_6$alkyl, $C_1$–$C_6$alkoxy, $C_1$–$C_6$haloalkyl, $C_1$–$C_6$haloalkoxy, nitro, cyano and/or the group

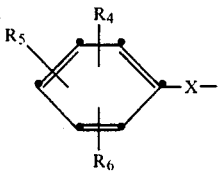

wherein

X is O, S, SO or $SO_2$;

$R_4$, $R_5$ and $R_6$ are each independently hydrogen, halogen, cyano, nitro, $C_1$–$C_6$alkyl, $C_1$–$C_6$alkoxy, $C_1$–$C_6$haloalkyl and/or $C_1$–$C_6$haloalkoxy;

and to the acid addition salts and metal complexes thereof.

An important subgroup of compounds of formula I comprises those wherein T is —C(O)— or —CH(OH)—, and a further important subgroup comprises those compounds of formula I wherein T is one of the groups

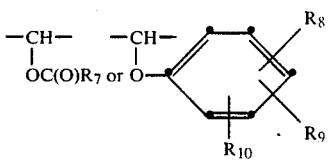

and the remaining substituents are as defined for formula I.

Depending on the indicated number of carbon atoms, alkyl by itself or as moiety of another substituent comprises e.g. the following groups: methyl, ethyl, propyl, butyl, pentyl, hexyl etc., and their isomers, e.g. isopropyl, isobutyl, tert-butyl, isopentyl etc. Haloalkyl denotes here a mono- to perhalogenated alkyl substituent, e.g. $CHCl_2$, $CHF_2$, $CH_2Cl$, $CCl_3$, $CH_2F$, $CH_2CH_2Cl$, $CHBr_2$ etc., preferably $CF_3$.

Throughout this specification, halogen denotes fluorine, chlorine, bromine or iodine, preferably fluorine, chlorine or bromine. Haloalkoxy denotes a mono- to perhalogenated alkoxy radical, e.g. $CF_3O$, $F_2CHO$, $FCH_2O$, $CF_3CF_2O$, $CCl_3CCl_2O$, $CHCl_2CCl_2O$, $CHCl_2CHClO$, $CHBr_2CH_2O$, $CH_2FCH_2O$ etc.

Accordingly, the present invention relates to the free organic compounds of the formula I and to the acid addition salts and metal complexes thereof. The free compounds are preferred, in particular to 1H-1,2,4-triazole derivatives falling within the scope of formula I.

Examples of salt-forming acids are inorganic acids, e.g. hydrohalic acids such as hydrofluoric acid, hydrochloric acid, hydrobromic acid or hydriodic acid, and also sulfuric acid, phosphoric acid, phosphorous acid, nitric acid; and organic acids such as acetic acid, trifluoroacetic acid, trichloroacetic acid, propionic acid, formic acid, benzenesulfonic acid, p-toluenesulfonic acid, methanesulfonic acid, maleic acid, succinic acid, tartaric acid, fumaric acid, salicylic acid, lactic acid or sorbic acid.

Metal complexes consist of the basic free compound of formula I and an inorganic or organic metal salt, for example the halides, nitrates, sulfates, phosphates, acetates, trifluoroacetates, trichloroacetates, propionates, tartrates, sulfonates, salicylates, benzoates etc. of the elements of the third and fourth main group of the Periodic Table such as aluminium, tin or lead, and of the first to eighth auxiliary group such as chromium, manganese, iron, cobalt, nickel, zirconium, copper, zinc, silver, mercury etc. Preferred elements are those of the auxiliary groups of the fourth period. The metals may exist in different valency states. The metal complexes of the formula I may be monocyclic or polycyclic, i.e. they can contain one or more parts of the organic molecule as ligands. Complexes with copper, zinc, manganese and tin are preferred.

The compounds of formula I are oils, resins or mainly solids which are stable at room temperature and have very valuable microbicidal properties. They can be used in agriculture or related fields preventively and curatively for controlling phytopathogenic microorganisms, for which utility the triazolylmethyl derivatives falling within the scope of formula I are preferred. The compounds of formula I exhibit very good fungicidal properties at low concentrations and their use poses no problems.

The following groups of compounds are preferred on account of their pronounced microbicidal, in particular fungicidal, activity:

(a) compounds of formula I,
wherein Az is 1H-1,2,4-triazole or 1H-imidazole; T is —C(O)— or —CH(OH)—; R is hydrogen or $C_1$-$C_6$alkyl; $R_1$ and $R_2$ are each independently hydrogen, halogen, $C_1$-$C_3$alkyl, $C_1$-$C_3$alkoxy, $C_1$-$C_3$haloalkyl, $C_1$-$C_3$haloalkoxy, nitro and/or cyano; and $R_3$ is hydrogen, halogen, $C_1$-$C_3$alkyl, $C_1$-$C_3$alkoxy, $C_1$-$C_3$haloalkyl, $C_1$-$C_3$haloalkoxy, nitro, cyano and/or the group

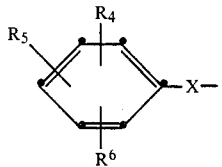

wherein X is O, S, SO or $SO_2$; $R_4$, $R_5$ and $R_6$ are each independently hydrogen, halogen, cyano, nitro, $C_1$-$C_3$alkyl, $C_1$-$C_3$alkoxy, $C_1$-$C_3$haloalkyl and/or $C_1$-$C_3$haloalkoxy; and the acid addition salts and metal complexes thereof;

(b) compounds of formula I,
wherein Az is 1H-1,2,4-triazole or 1H-imidazole; T is —C(O)— or —CH(OH)—; R is hydrogen or $C_1$-$C_6$alkyl; $R_1$ and $R_2$ are each independently hydrogen, fluorine, chlorine, bromine, methyl, ethyl, methoxy, ethoxy, $CF_3$, $C_1$-$C_2$haloalkyl, nitro and/or cyano; $R_3$ is hydrogen, fluorine, chlorine, bromine, methyl, methoxy, $CF_3$, $OCHF_2$, $OCF_3$, nitro, cyano and/or the group

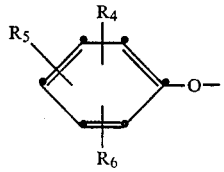

wherein $R_4$ is hydrogen; and $R_5$ and $R_6$ are each independently hydrogen, fluorine, chlorine, bromine, methyl, ethyl, methoxy, ethoxy, $CF_3$ and/or $OCHF_2$; and the acid addition salts and metal complexes thereof;

(c) compounds of formula I, wherein T is —C(O)— and the substituents R to $R_6$ are as defined for group b;

(d) compounds of formula I,
wherein T is —CH(OH)— and the substituents R to $R_6$ are as defined for group b;

(e) compounds of formula I
wherein T is —C(O)— or —CH(OH)—; Az is 1H-1,2,4-triazole; R is hydrogen or $C_1$-$C_4$alkyl; $R_1$ and $R_2$ are each independently hydrogen, fluorine, chlorine, bromine, methyl, methoxy, $CF_3$, $OCHF_2$, $OCF_3$, nitro and/or cyano; and $R_3$ is the group

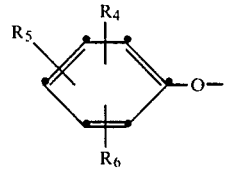

wherein $R_4$, $R_5$ and $R_6$ are each independently hydrogen, fluorine, chlorine, bromine, methyl, methoxy, $CF_3$, $OCF_3$, $OCHF_2$, cyano and/or nitro; and the acid addition salts and metal complexes thereof;

(f) compounds of formula I,
wherein T is —C(O)— or —CH(OH)—; Az is 1H-1,2,4-triazole; R is hydrogen or $C_1$-$C_4$alkyl; $R_1$ is in ortho-position and $R_2$ is in para-position and each is independently fluorine, chlorine, bromine, methyl, methoxy, $CF_3$, $OCHF_2$, $OCF_3$, nitro or cyano; and $R_3$ is hydrogen; and the acid addition salts and metal complexes thereof;

(g) compounds of formula I,
wherein T is —C(O)— or —CH(OH)—; Az is 1H-1,2,4-triazole; R is hydrogen or $C_1$-$C_4$alkyl; $R_3$ is the group

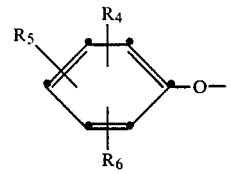

wherein $R_1$, $R_2$, $R_4$, $R_5$ and $R_6$ are each independently hydrogen, fluorine, chlorine, bromine, methyl, methoxy, $CF_3$, $OCF_3$, $OCHF_2$, cyano and/or nitro; and the acid addition salts and metal complexes thereof.

Examples of particularly preferred alkanones within the scope of formula I are:

1-(2,4-dichlorophenyl)-2-fluoro-2-(1H-1,2,4-triazol-1-yl)ethanone (1.1);

1-(2,4-dichlorophenyl)-2-fluoro-2-(1H-imidazol-1-yl)ethanone (1.2);

1-(2,4-dichlorophenyl)-2-fluoro-2-(1H-1,2,4-triazol-1-yl)propanone (1.3);

1-(2,4-dichlorophenyl)-2-fluoro-2-(1H-imidazol-1-yl)propanone (1.4);

1-(2,4-dichlorophenyl)-2-fluoro-2-(1H-1,2,4-triazol-1-yl)butanone (1.5);

1-(phenyl)-2-fluoro-2-(1H-1,2,4-triazol-1-yl)ethanone (1.9);

1-(phenyl)-2-fluoro-2-(1H-1,2,4-triazol-1-yl)propanone (1.10);

1-(1-(phenyl)-2-fluoro-2-(1H-1,2,4-triazol-1-yl)hexanone (1.11);

1-(2,4-dichlorophenyl)-2-fluoro-2-(1H-1,2,4-triazol-1-yl)pentanone (1.12);
1-(4-fluorophenyl)-2-fluoro-2-(1H-1,2,4-triazol-1-yl)hexanone (1.15);
1-(4-chlorophenyl)-2-fluoro-2-(1H-1,2,4-triazol-1-yl)ethanone (1.18);
1-(3,4-dichlorophenyl)-2-fluoro-2-(1H-1,2,4-triazol-1-yl)ethanone (1.23);
1-(2,5-dichlorophenyl)-2-fluoro-2-(1H-1,2,4-triazol-1-yl)ethanone (1.25);
1-(2,4-dimethylphenyl)-2-fluoro-2-(1H-1,2,4-triazol-1-yl)ethanone (1.27);
1-(4-bromophenyl)-2-fluoro-2-(1H-1,2,4-triazol-1-yl)ethanone (1.28);
1-(2,4-difluorophenyl)-2-fluoro-2-(1H-1,2,4-triazol-1-yl)ethanone (1.56);
1-(2,3,4-trichlorophenyl)-2-fluoro-2-(1H-1,2,4-triazol-1-yl)ethanone (1.57);
1-(3-methoxyphenyl)-2-fluoro-2-(1H-1,2,4-triazol-1-yl)ethanone (1.60);
1-(2-methoxyphenyl)-2-fluoro-2-(1H-1,2,4-triazol-1-yl)ethanone (1.61);
1-[4-(4-chlorophenoxy)phenyl]-2-fluoro-2-(1H-1,2,4-triazol-1-yl)ethanone (3.6);
1-[4-(4-chlorophenoxy)phenyl]-2-fluoro-2-(1H-1,2,4-triazol-1-yl)propanone (3.10);
1-[4-(2,4-dichlorophenoxy)phenyl]-2-fluoro-2-(1H-1,2,4-triazol-1-yl)ethanone (3.12);
1-[4-(2,4-dichlorophenoxy)phenyl]-2-fluoro-2-(1H-1,2,4-triazol-1-yl)propanone (3.16);

Among these alkanones, compounds 1.1, 1.3 and 1.12 are particularly preferred.

Examples of particularly preferred alkanols within the scope of formula I are:
1-(2,4-dichlorophenyl)-2-fluoro-2-(1H-1,2,4-triazol-1-yl)ethanol (2.1);
1-(2,4-dichlorophenyl)-2-fluoro-2-(1H-1,2,4-triazol-1-yl)propanol (2.3);
1-(2,4-dichlorophenyl)-2-fluoro-2-(1H-imidazol-1-yl)propanol (2.4);
1-(2,4-dichlorophenyl)-2-fluoro-2-(1H-1,2,4-triazol-1-yl)butanol (2.5);
1-(phenyl)-2-fluoro-2-(1H-1,2,4-triazol-1-yl)ethanol (2.9);
1-(phenyl)-2-fluoro-2-(1H-1,2,4-triazol-1-yl)propanol (2.10);
1-(phenyl)-2-fluoro-2-(1H-1,2,4-triazol-1-yl)hexanol (2.11);
1-(2,4-dichlorophenyl)-2-fluoro-2-(1H-1,2,4-triazol-1-yl)pentanol (2.12);
1-(2,4-dichlorophenyl)-2-fluoro-2-(1H-imidazol-1-yl)butanol (2.13);
1-(4-fluorophenyl)-2-fluoro-2-(1H-1,2,4-triazol-1-yl)ethanol (2.14);
1-(4-chlorophenyl)-2-fluoro-2-(1H-1,2,4-triazol-1-yl)ethanol (2.17);
1-(3,4-dichlorophenyl)-2-fluoro-2-(1H-1,2,4-triazol-1-yl)ethanol (2.22);
1-(2,5-dichlorophenyl)-2-fluoro-2-(1H-1,2,4-triazol-1-yl)ethanol (2.24);
1-(2,4-dimethylphenyl)-2-fluoro-2-(1H-1,2,4-triazol-1-yl)ethanol (2.27);
1-(4-bromophenyl)-2-fluoro-2-(1H-1,2,4-triazol-1-yl)ethanol (2.28);
1-(2,4-difluorophenyl)-2-fluoro-2-(1H-1,2,4-triazol-1-yl)ethanol (2.56);
1-(2,3,4-trichlorophenyl)-2-fluoro-2-(1H-1,2,4-triazol-1-yl)ethanol (2.57);
1-(3-methoxyphenyl)-2-fluoro-2-(1H-1,2,4-triazol-1-yl)ethanol (2.60);
1-(2-methoxyphenyl)-2-fluoro-2-(1H-1,2,4-triazol-1-yl)ethanol (2.61);
1-[4-(4-chlorophenoxy)phenyl]-2-fluoro-2-(1H-1,2,4-triazol-1-yl)ethanol (3.7);
1-[4-(4-chlorophenoxy)phenyl]-2-fluoro-2-(1H-1,2,4-triazol-1-yl)propanol (3.11);
1-[4-(2,4-dichlorophenoxy)phenyl]-2-fluoro-2-(1H-1,2,4-triazol-1-yl)ethanol (3.13; 3.14; 3.15);
1-[4-(2,4-dichlorophenoxy)phenyl]-2-(1H-1,2,4-triazol-1-yl)propanol (3.17);
1-[4-(4-chlorophenoxy)-2-methylphenyl]-2-fluoro-2-(1H-1,2,4-triazol-1-yl)ethanol (3.30).

Particularly preferred are the alkanols 2.1 and 2.5.

Particularly preferred subgroups of microbicidal ethers comprise e.g. the following compounds of formula I (h) compounds of formula I,
wherein Az is 1H-1,2,4-triazole or 1H-imidazole; T is one of the groups

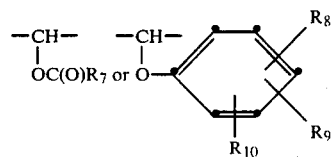

wherein $R_7$ is $C_1$–$C_6$alkyl, or is $C_1$–$C_4$alkyl which is substituted by fluorine, chlorine, bromine or $C_1$–$C_2$alkoxy, or is $C_3$–$C_4$alkenyl, $C_3$–$C_4$alkynyl, cyclopropyl, cyclohexyl, 2-furyl, 2-tetrahydrofuryl, or is phenyl or benzyl, each unsubstituted or substituted by fluorine, chlorine, bromine, nitro, methyl, methoxy, $CF_3$, $OCF_3$ and/or $OCHF_2$; $R_8$, $R_9$ and $R_{10}$ are each independently hydrogen, nitro, fluorine, chlorine, bromine, methyl, cyano, methoxy, —$COOCH_3$, $CF_3$, $NH_2$ or $NHCOCH_3$; R is hydrogen or $C_1$–$C_6$alkyl; $R_1$ and $R_2$ are each independently hydrogen, halogen, $C_1$–$C_3$alkyl, $C_1$–$C_3$alkoxy, $C_1$–$C_3$haloalkyl, $C_1$–$C_3$haloalkoxy, nitro and/or cyano; and $R_3$ is hydrogen, halogen, $C_1$–$C_3$alkyl, $C_1$–$C_3$alkoxy, $C_1$–$C_3$haloalkyl, $C_1$–$C_3$haloalkoxy, nitro, cyano, and/or the group

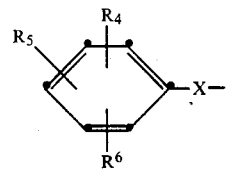

wherein X is O, S, SO or $SO_2$; $R_4$, $R_5$ and $R_6$ are each independently hydrogen, halogen, cyano, nitro, $C_1$–$C_3$alkyl, $C_1$–$C_3$alkoxy, $C_1$–$C_3$haloalkyl and/or $C_1$–$C_3$haloalkoxy; and the acid addition salts and metal complexes thereof;

(i) compounds of formula I,
wherein Az is 1H-1,2,4-triazole or 1H-imidazole; T is one of the groups

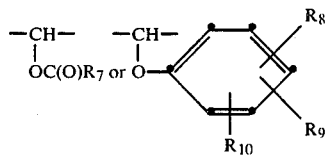

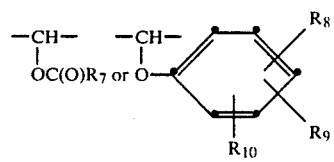

wherein $R_7$ is $C_1$–$C_6$alkyl, or is $C_1$–$C_4$alkyl which is substituted by fluorine, chlorine, bromine or $C_1$–$C_2$alkoxy, or is $C_3$–$C_4$alkenyl, $C_3$–$C_4$alkynyl, cyclopropyl, cyclohexyl, 2-furyl, 2-tetrahydrofuryl, or is phenyl or benzyl, each unsubstituted or substituted by fluorine, chlorine, bromine, nitro, methyl, methoxy, $CF_3$, $OCF_3$ and/or $OCHF_2$; $R_8$, $R_9$ and $R_{10}$ are each independently hydrogen, nitro, fluorine, chlorine, bromine, methyl, cyano, methoxy, —$COOCH_3$, $CF_3$, $NH_2$ or $NHCOCH_3$; R is hydrogen or $C_1$–$C_6$alkyl; $R_1$ and $R_2$ are each independently hydrogen, fluorine, chlorine, bromine, methyl, ethyl, methoxy, ethoxy, $CF_3$, $C_1$–$C_2$-haloalkyl, nitro and/or cyano; $R_3$ is hydrogen, fluorine, chlorine, bromine, methyl, methoxy, $CF_3$, $OCHF_2$, $OCF_3$, nitro, cyano and/or the group wherein $R_7$ is $C_1$–$C_6$alkyl, or is $C_1$–$C_4$alkyl which is substituted by fluorine, chlorine, bromine or $C_1$–$C_2$alkoxy, or is $C_3$–$C_4$alkenyl, $C_3$–$C_4$alkynyl, cyclopropyl, cyclohexyl, 2-furyl, 2-tetrahydrofuryl, or is phenyl or benzyl, each unsubstituted or substituted by fluorine, chlorine, bromine, nitro, methyl, methoxy, $CF_3$, $OCF_3$ and/or $OCHF_2$; $R_8$, $R_9$ and $R_{10}$ are each independently hydrogen, nitro, fluorine, chlorine, bromine, methyl, cyano, methoxy, —$COOCH_3$, $CF_3$, $NH_2$ or $NHCOCH_3$; Az is 1H-1,2,4-triazole; R is hydrogen or $C_1$–$C_4$alkyl; $R_1$ and $R_2$ are each independently hydrogen, fluorine, chlorine, bromine, methyl, methoxy, $CF_3$, $OCHF_2$, $OCF_3$, nitro and/or cyano; and $R_3$ is the group

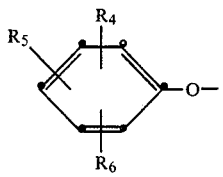

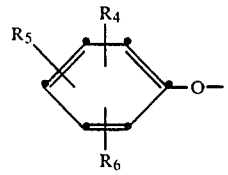

wherein $R_4$ is hydrogen; and $R_5$ and $R_6$ are each independently hydrogen, fluorine, chlorine, bromine, methyl, ethyl, methoxy, ethoxy, $CF_3$ and/or $OCHF_2$; and the acid addition salts and metal complexes thereof;

(k) compounds of formula I,
wherein T is the group

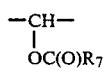

wherein $R_7$ is $C_1$–$C_6$alkyl, or is $C_1$–$C_4$alkyl which is substituted by fluorine, chlorine, bromine or $C_1$–$C_2$alkoxy, or is $C_3$–$C_4$alkenyl, $C_3$–$C_4$alkynyl, cyclopropyl, cyclohexyl, 2-furyl, 2-tetrahydrofuryl, or is phenyl or benzyl, each unsubstituted or substituted by fluorine, chlorine, bromine, nitro, methyl, methoxy, $CF_3$, $OCF_3$ and/or $OCHF_2$; and the substituents R to $R_6$ are as defined for group b;

(l) compounds of formula I,
wherein T is the group

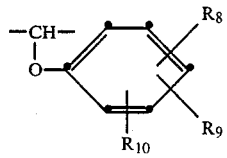

wherein $R_8$, $R_9$ and $R_{10}$ are each independently hydrogen, nitro, fluorine, chlorine, bromine, methyl, cyano, methoxy, —$COOCH_3$, $CF_3$, $NH_2$ or $NHCOCH_3$; and the substituents R to $R_6$ are as defined for group b;

(m) compounds of formula I,
wherein T is one of the groups wherein $R_4$, $R_5$ and $R_6$ are each independently hydrogen, fluorine, chlorine, bromine, methyl, methoxy, $CF_3$, $OCF_3$, $OCHF_2$, cyano and/or nitro; and the acid addition salts and metal complexes thereof.

Among the compounds of groups h to m, those compounds are particularly preferred wherein $R_1$ is in the 2-position and $R_2$ is the 4-position of the phenyl ring and $R_3$ is hydrogen; and among these compounds, those compounds are particularly preferred wherein $R_1$ and $R_2$ are halogen, preferably chlorine or fluorine.

(n) compounds of formula I,
wherein Az is 1H-1,2,4-triazole; T is one of the groups wherein $R_7$ is $C_1$–$C_4$alkyl, or is phenyl which is unsubstituted or substituted by fluorine, chlorine, bromine, nitro, methyl, methoxy, $CF_3$, $OCF_3$ and/or $OCHF_2$; $R_8$, $R_9$ and $R_{10}$ are each independently hydrogen, fluorine, chlorine, bromine, nitro, methyl, methoxy, $CF_3$, $OCF_3$ or $OCHF_2$; R is hydrogen or $C_1$–$C_4$alkyl; $R_1$ is in the ortho-position, $R_2$ is in the meta-position and each is independently fluorine, chlorine, bromine, methyl, methoxy, $CF_3$, $OCHF_2$, nitro or cyano; and $R_3$ is hydrogen.

Examples of particularly preferred ethers and esters within the scope of formula I are:
1-(2,4-dichlorophenyl)-1-acetoyl-2-fluoro-2-(1H-1,2,4-triazol-1-yl)ethane, (5.1), 1-(2,4-dichlorophenyl)-1-benzoyl-2-fluoro-2-(1H-1,2,4-triazol-1-1,2,4-triazol-1-yl)ethane, (5.15), 1-(2,4-dichlorophenyl)-1-(4-nitrophenoxy)-2-fluoro-2-(1H-1,2,4-triazol-1-yl)ethane (6.1).

It has been found that compounds of formula I and the acid addition salts and metal complexes thereof are obtained by reacting a ketone of formula II

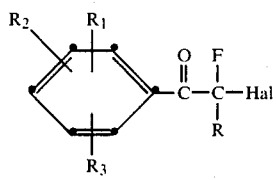

wherein R, $R_1$, $R_2$ and $R_3$ are as defined for formula I and Hal is halogen, preferably chlorine or bromine, with an azole of formula III

 (III)

wherein Az is as defined for formula I and Me is hydrogen, a metal cation, preferably an alkali metal or alkaline earth metal cation (e.g. $Na^+$, $K^+$, $Ca^{2+}$ etc.) or a tetraalkylammonium ion, preferably a tetra-lower alkylammonium ion, e.g. $n(C_4H_9\text{---}n)^+$, to give an alkanone of formula Ia

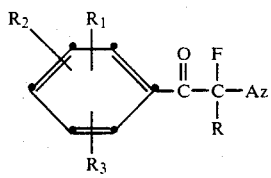

wherein the substituents are as defined for formula I, and optionally reducing the alkanone of formula Ia in generally known manner to give an alkanol of formula Ib

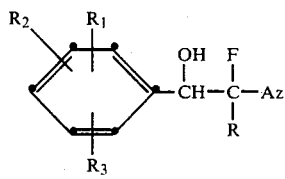

wherein the substituents are as defined for formula I, and then optionally adding an acid or a metal salt to the compounds of formula I, or esterifying the alkanol of formula Ib by reaction with a compound of formula IV

 (IV)

wherein Y is hydroxy, alkoxy (preferably $C_1$-$C_6$alkoxy), $R_7C(O)O\text{---}$ or halogen, preferably chlorine or bromine, and $R_7$ is as defined for formula I, and the ethers of formula I are obtained by reacting an alkanol of formula Ib above with a compound of formula V

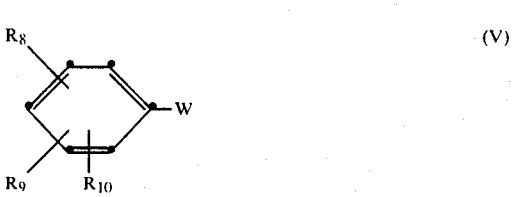

and optionally converting a compound obtainable by a process of this invention into another compound of formula I by reduction, conversion or by exchange of a substituent, in which formula V above $R_8$, $R_9$ and $R_{10}$ are as defined for formula I and W is OH or a customary leaving group, by which is meant throughout this specification substituents such as halogens [e.g. fluorine, chlorine, bromine or iodine, preferably chlorine or bromine]; sulfonyloxy groups, preferably $\text{---}OSO_2\text{---}R_a$; acyloxy groups, preferably $\text{---}OCO_2\text{---}R_a$; isourea radicals, preferably $$-O-\underset{NHR_c}{C}=NR_b;$$

where $R_a$, $R_b$ and $R_c$ are each independently $C_1$-$C_3$alkyl, $C_1$-$C_3$haloalkyl, or are phenyl which is unsubstituted or substituted by halogen, methyl, nitro, trifluoromethyl and/or methoxy.

In such cases where phenyl ethers of formula I are to be prepared wherein the phenyl group in the ether function contains an electrophilic radical in the 2- or 4-position, e.g. $NO_2$, CN, COOalkyl etc., said radical can readily be converted by reduction ($NO_2 \rightarrow NH_2$) or exchange (e.g. replacement by halogen) into another substituent ($R_8$ to $R_{10}$) to give compounds of formula I which are substituted in the 2- or 4-position and are otherwise only obtainable in insufficient yield.

The process is carried out in the absence or preferably in the presence of an inert solvent. Accordingly the reaction of II with III is preferably carried out in a relatively polar, but inert, organic solvent, e.g. N,N-dimethylformamide, N-N-dimethylacetamide, dimethylsulfoxide, in nitriles such as acetonitrile, benzonitrile, propionitrile etc., in ketones such as acetone, methylethyl ketone etc., in ethereal solvents such as tetrahydrofuran or dioxan and others. Such solvents may be employed in combination with other conventional inert solvents such as aliphatic or aromatic hydrocarbons, e.g. benzene, toluene, xylene, hexane, petroleum ether, chlorobenzene, nitrobenzene etc. The reaction is carried out in the temperature range from 0° to 150° C., preferably from 20° to 100° C. under normal pressure, optionally under increased pressure.

The reaction is conveniently conducted in the presence of a condensing agent or of an acid acceptor. Examples of such compounds are organic and inorganic bases, e.g. tertiary amines such as trialkylamines (trimethylamine, triethylamine, tripropylamine etc.), pyridine and pyridine bases (4-dimethylaminopyridine, 4-pyrrolidylaminopyridine etc.), oxides, hydrides and hydroxides, carbonates and bicarbonates of alkali metals and alkaline earth metals (CaO, BaO, NaOH, LiOH, KOH, NaH, $Ca(OH)_2$, $KHCO_3$, $NaHCO_3$, $Ca(HCO_3)_2$, $K_2CO_3$, $Na_2CO_3$), as well as alkali metal acetates such as $CH_3COONa$ or $CH_3COOK$. Also suitable are alkali alcoholates such as $C_2H_5ONa$, $C_3H_7\text{---}nONa$ etc. In some cases it may be advantageous to convert the free azole of formula III (M=hydrogen) first—e.g. in situ with an alcoholate—into the corresponding salt, and then to react this latter with the ketone of formula II in the presence or absence of one of the bases specified above. Parallel to the formation of the 1,2,4-triazolyl derivatives, there are usually also obtained 1,3,4-triazolyl isomers, which can be separated from one another in conventional manner, e.g. with different solvents. Nascent hydrogen halide can in some cases also be expelled from the reaction mixture by introducing inert gas, e.g. nitrogen, or by addition of a molecular sieve.

The reduction of this invention (Ia to Ib) is carried out in a manner known per se, e.g. by reaction with metal hydrides such as LiAlH$_4$, NaBH$_4$, BH$_3$ etc. (q.v. H. O. House, "Modern Synthetic Reactions", 1972, p. 45 ff. and p. 154). If the reaction is carried out with metal hydrides, suitable diluents for the reduction of this invention are polar organic solvents. Where the metal hydride is NaBH$_4$, then suitable solvents are e.g. lower alkanols such as methanol, ethanol, butanol or isopropanol, otherwise ethers such as dialkyl ethers, e.g. diethyl ether or tetrahydrofuran. The reduction is generally carried out in the temperature range from 0° to 30° C., preferably from 0° to 20° C. In this reduction about 1 reaction equivalent of a metal hydride such as sodium borohydride or lithium aluminium hydride is used per 1 mole of the ketone of formula Ia. To isolate the reduced compounds of formula Ib, the residue is taken up in dilute hydrochloric acid, then made alkaline and extracted with an organic solvent. Further working up is by conventional methods.

If the reduction is carried out with aluminium isopropylate, suitable diluents are preferably alkanols such as isopropanol, or conventional inert hydrocarbons such as benzene or toluene. In this process too, the reaction temperatures may also vary within a wide range; the reduction is generally carried out in the temperature range from 20° to 120° C., preferably from 50° to 100° C. In this reduction about 1 to 2 moles of aluminium isopropylate are used per 1 mole of ketone of the formula Ia. To isolate the reduced compounds of formula Ib, excess solvent is removed by vacuum distillation and the resultant aluminium compound is decomposed with dilute sulfuric acid or NaOH solution. Further working up is by conventional methods.

The azoles of formula III are generally known compounds.

The α-halo-α-fluoroketones II are either known [q.v. F. Bergmann et al., J. Am. Chem. Soc. 79, 4178 (1957)] or can be prepared by methods known per se, e.g. by conventional halogenation of the corresponding α-fluoroketones of formula IV

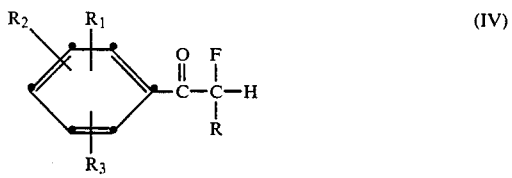

wherein the substituents are as defined for formula I. The α-fluoroketones are either known [q.v. Houben-Weil, Volume 5/3, pp. 211, 246 and 494, and F. Bergmann et al., J. Am. Chem. Soc. 76, 4137 (1954)] or they can be obtained by methods analogous to those for obtaining the known α-fluoroketones from corresponding known α-bromoketones by conventional exchange of bromine for fluorine or can be prepared by acylating the corresponding aromatic compound with fluorinated carboxylic acid derivatives, e.g. by the Friedel-Crafts process.

Acid addition salts of formula I can be obtained in simple manner by conventional methods of salt formation, e.g. by dissolving a compound of formula I in a suitable inert solvent and adding the appropriate acid. e.g. a hydrohalic acid such as HCl, and can be isolated in known manner, e.g. by filtration, and, if desired, be purified by washing with an inert organic solvent.

For the preparation of metal complexes of formula I, suitable salts are preferably salts of those anions and cations which have already been cited as preferred in connection with the description of the metal complexes of this invention.

The metal complexes of formula I can be obtained in simple manner by conventional methods, e.g. by dissolving the metal salt in an alcohol, e.g. ethanol, and adding the solution to the free compound of formula I. The metal complexes can be isolated in known manner, e.g. by filtration, and e.g. be purified by recrystallisation.

Inert solvents or diluents can be used in the etherification and esterification reactions described. Suitable inert solvents or diluents are e.g. aliphatic and aromatic hydrocarbons such as benzene, toluene, xylenes, petroleum ether; halogenated hydrocarbons such as chlorobenzene, methylene chloride, ethylene chloride, chloroform, carbon tetrachloride, tetrachloroethylene; ethers and ethereal compounds such as dialkyl ethers (dialkyl ether, diisopropyl ether, tert-butylmethyl ether etc.), anisole, dioxan, tetrahydrofuran; nitriles such as acetonitile, propionitrile; N,N-dialkylated amides such as dimethylformamide; dimethylsulfoxide; ketones such as acetone, diethyl ketone, and mixtures of such solvents. In some cases the acylating or etherifying agent itself can be used as solvent.

Preferred solvents are ethers, acetone, chloroform, dioxan, dimethylformamide and dimethylsulfoxide.

In the esterification of Ib and IV to I the presence of a catalyst such as dimethylformamide can be advantageous.

For the etherification and esterification, the reaction temperatures are in the range from 0° to 180° C., preferably from 10° to 80° C. or at the boiling point of the solvents or mixture of solvents. In some cases the use of acid acceptors or condensing agents is advantageous. Examples of such compounds are organic and inorganic bases, e.g. tertiary amines such as trialkylamines (trimethylamine, triethylamine, tripropylamine etc.), pyridine and pyridine bases (4-dimethylaminopyridine, 4-pyrrolidiylaminopyridine etc.), oxides, hydroxides, carbonates and bicarbonates of alkali metals and alkaline earth metals and alkali metal acetates (KOH, NaOH, Na$_2$CO$_3$, NaHCO$_3$, CaO, Ca(OH)$_2$, Ba(OH)$_2$, NaOC(O)CH$_3$).

Nascent hydrogen halide can in some cases also be expelled from the reaction mixture by introducing inert gas, e.g. nitrogen, or by addition of a molecular sieve.

The further reaction of Ib with V, where W in formula V is a customary leaving group, is carried out in the absence or preferably in the presence of one of the inert solvents above. It is also possible to use mixtures of these solvents with each other or with other customary inert organic solvents, e.g. with aromatic hydrocarbons such as benzene, toluene, xylenes and the like. It can sometimes also be advantageous to convert the alkanol of formula Ib first into a suitable metal salt in a manner known per se, e.g. by reaction with a strong base.

Examples of suitable strong bases are alkali metal and alkaline earth metal hydrides (NaH, KH, CaH$_2$ and the like) and organic alkaline compounds such as butyllithium or alkali tert-butoxide. Further, it is also possible to use alkali metal hydroxides such as NaOH or KOH if the process is carried out in an aqueous two-phase system and in the presence of a phase transfer catalyst.

However, before the further reaction, the alkanol of formula Ia can also be converted into an alkali metal alcoholate and then reacted with a compound of formula V (wherein W is a leaving group), in which case the reaction is conveniently carried out in the presence of a crown ether. The preferred crown ethers are 18-crown-6 (where M=K) and 15-crown-5 (where M=Na). The reaction is advantageously conducted in an inert medium. Examples of suitable solvents are ethers and ethereal compounds, e.g. di-lower alkyl ethers (diethyl ether, diisopropyl ether, tert-butylmethyl and the like), tetrahydrofuran, dioxan and aromatic hydrocarbons such as benzene, toluene or xylenes.

The following solvents for example are suitable for the organic water-immiscible phase: aliphatic and aromatic hydrocarbons such as pentane, hexane, cyclohexane, petroleum ether, ligroin, benzene, toluene, xylenes etc.; halogenated hydrocarbons such as dichloromethane, chloroform, carbon tetrachloride, ethylene dichloride, 1,2-dichloroethane, tetrachloroethylene and the like, or aliphatic ethers such as diethyl ether, diisopropyl ether, tert-butylmethyl ether etc. Examples of suitable phases transfer catalysts are: tetraalkylammonium halides, hydrogen sulfates or hydroxides, e.g. tetrabutylammonium chloride, tetrabutylammonium bromide, tetrabutylammonium iodide, triethylbenzylammonium chloride or triethylbenzylammonium bromide, tetrapropylammonium chloride, tetrapropylammonium bromide or tetrapropylammonium iodide etc. Suitable phase transfer catalysts are also phosphonium salts. The reaction temperatures are generally in the range from 30° to 130° C. or at the boiling point of the solvent or mixture of solvents.

Where W in formula V is hydroxy, it is advantageous to carry out a condensation reaction. Both reactants are heated under reflux in a suitable solvent.

For the above reaction it is in principle possible to use solvents which are inert to the reactants and conveniently form azeotropes with water. Examples of such solvents are aromatic hydrocarbons such as benzene, toluene, xylenes or halogenated hydrocarbons such as dichloromethane, chloroform, carbon tetrachloride, 1,2-dichloroethane, tetrachloroethylene, chlorobenzene, and also ethereal compounds such as tert-butylmethyl ether, dioxan and the like. In some cases the compound of formula III itself can be used as solvent. This condensation reaction is advantageously carried out in the presence of a strong acid, e.g. paratoluenesulfonic acid, and at the boiling temperatures of the mixture of azeotropes.

To prepare the ethers of the formula I, it is also possible to replace the free OH group in the compound of formula Ib first by one of the above mentioned customary leaving groups W, and then to carry out a conversion reaction with a compound of the formula V (W=OH).

The replacement of the free hydroxyl group in the compounds of formula Ib by a leaving group W is preferably carried out in an inert solvent. Examples of such solvents are: aromatic and aliphatic hydrocarbons such as benzene, toluene, xylenes, petroleum ether, ligroin or cyclohexane; halogenated hydrocarbons such as chlorobenzene, methylene chloride, ethylene chloride, chloroform, carbon tetrachloride or tetrachloroethylene; ethers and ethereal compounds such as diethyl ether, diisopropyl ether, tert-butylmethyl ether, dimethoxyethane, dioxan, tetrahydrofuran or anisole; esters such as ethyl acetate, propylacetate or butylacetate; nitriles such as acetonitrile; or compounds such as dimethylsulfoxide, dimethylformamide and mixtures of such solvents.

The above described preparatory process, including all variants, constitutes an object of the present invention.

The starting materials of formulae IV and V are generally known or can be prepared by methods known per se.

Compounds of formula I

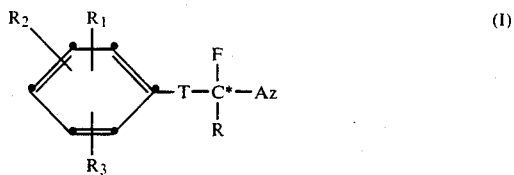

always contain an asymmetrical carbon atom (*) vicinal to the function T and can therefore be obtained in the form of two enantiomers. Normally a mixture of both enantiomers is obtained in the preparation of these substances, which mixture can be resolved in conventional manner into the pure optical antipodes, e.g. by fractional crystallisation of salts with optically active strong acids. The enantiomers can have different biological properties. For example, the one enantiomer can principally have leaf-fungicidal properties and the other principally soil-fungicidal properties. There may also be a graduated difference in activity while the activity spectrum remains the same. Where T=—*CH(OH)—, the compounds of formula I contain a further centre of asymmetry (*) resulting in the formation of mixtures of diastereoisomers (theo and erythro forms) which may be separated by physical methods. The individual isomers differ as follows:

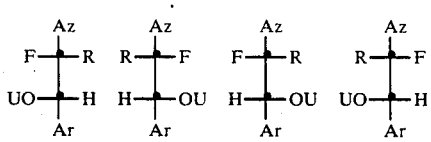

wherein Ar is the group

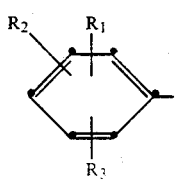

and U is OH, —C(O)R$_7$ or

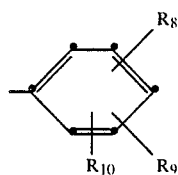

and the remaining substituents are as defined for formula I.

The present invention relates to all pure enantiomers, diastereoisomers and mixtures thereof.

The above described preparatory process, indlucing all partial steps, constitutes an important object of the present invention.

Triazolyl alkanones and triazolyl alkanols of the general formula X

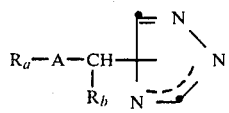

wherein $R_a$=alkyl, cycloalkyl, aryl or substituted aryl;

$R_b$=hydrogen, alkyl, cycloalkyl, aryl or substituted aryl;

$R_a+R_b$=an aliphatic ring; and

A=—C(O)— or —CH(OH)—, are described in German Offenlegungsschrift No. DE-2 431 407 as fungicides in particular against fungi of the species Erysiphe, Podosphaera, Venturia and Fusicladium.

Surprisingly, it has now been found that the introduction of a fluorine atom into the methylene group vicinal to the azole group leads to a significant shift in the activity spectrum. In contradistinction to the compounds disclosed in No. DE-2 431 407, the fluorinated compounds of formula I of the present invention exhibit an additional pronounced activity against Piricularia species, in particular against *Piricularia oryzae* (rice blast). The pathogen, the fungus *Piricularia oryzae*, belongs to the Fungi imperfecti and forms as fructification organs only conidiospores, namely an asexual secondary fruit form. *Piricularia oryzae* is one of the economically most important pests in rice crops since it attacks the rice plants in all stages of growth (seedlings, leaves, stems, ears etc.) and during the entire growth period. Depending on the cite attacked by the fungus and the stage in which the rice plants are at the time of infection, various terms are used to denote the disease: e.g. leaf blast denoting leaf specks which can lead to the necrosis of the leaves and thus to interrupted growth; ear blast denoting infections of the panicle or parts of the panicle; neck blast denoting attack on the panicle base, whereby the panicle breaks and no or only abnormal grains are formed; node blast denoting the breaking of stalks at the nodes. *Piricularia oryzae* spreads through conidiospores which multiply profusely under moist weather conditions and are transported by the wind over-wide areas. In areas where the cultivation of rice is interrupted over extended periods of time in the course of one year, at the beginning of the growing season conidiospores form on seedlings of infected seed, on crop remnants, on straw stacked in the fields and on infected grass. If rice is cultivated throughout the year, crops of different ages will be found beside each other, thus facilitating the transmission of disease by the constantly multiplying conidia. Piricularia infestation generally leads to very high crop losses and in view of the fact that at present, after wheat and maize, rice covers the third largest crop area among cereal crops, it results in very substantial economic damage.

Piricularia infestation can be successfully and simply controlled in all stages of growth with compounds of formula I. In addition, the compounds of formula I are also effective against the phytopathogenic fungi belonging to the following classes: Fungi imperfecti (e.g. Botrytis, Helminthosporium, Fusarium, Septoria, Cercospora and Alternaria); Basidiomycetes (e.g. the genera Hemileia, Rhizocotonia, Puccinia); Ascomycetes (e.g. Venturia, Podosphaera, Erysiphe, Monilinia, Uncinula). Furthermore, the compounds of formula I have a systemic action. They can also be used as seed dressing agents for protecting seeds (fruit, tubers, grains) and plant cuttings against fungus infections as well as against phytopathogenic fungi which occur in the soil.

Furthermore, compounds of formula I can be successfully used for protecting perishable goods of vegetable or animal origin. They control mould fungi such as Penicillium, Aspergillus, Rhizopus, Fusarium, Helminthosporium, Nigrospora and Alternaria, as well as bacteria such as butyric acid bacteria and yeast fungi such as Candida.

The compounds of formula I can therefore be used in storage protection (e.g. cereals, silage, hay etc.).

The compounds of formula I have thus for practical purposes a very useful microbicidal spectrum against phytopathogenic fungi and bacteria. The compounds of formula I have in particular very advantageous preventive and additionally systemic action and can be used for protecting numerous cultivated plants, preferably rice crops. It is possible to inhibit or destroy the microorganisms which occur in plants or parts of plants (fruit, blossoms, leaves, stems, tubers, roots) in different crops of useful plants with the compounds of formula I, while at the same time the parts of plants which grow later are also protected from attack by such microorganisms.

Accordingly, the invention also relates to microbicidal compositions and to the use of compounds of the formula I for controlling phytopathogenic microorganisms, especially harmful fungi, and in particular for the preventive andd systemic treatment of plants to protect them from attack by such microorganisms.

The invention further embraces the preparation of agrochemical compositions which comprises homogeneously mixing the active ingredient with one or more compounds or groups of compounds described herein. The invention furthermore relates to a method of treating plants, which comprises applying thereto the compounds of the formula I or the novel compositions.

In addition to the principal crop rice, target grops to be protected within the scope of the present invention comprise e.g. the following species of plants:

cereals (wheat, barley, rye, oats, sorghum and related crops), beet (sugar beet and fodder beet), drupes, pomes and soft fruit (apples, pears, plums, peaches, almonds, cherries, strawberries, rasberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fibre plants (cotton, flax, hemp, jute), citrus fruit (oranges, lemons, grapefuit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (composites).

The compounds of formula I are normally applied in agriculture the form of compositions and can be applied to the crop area or plant to be treated, simultaneously or in succession, with further compounds. These compounds can be both fertilisers or micronutrient donors or other preparations that influence plant growth. They can also be selective herbicides, insecticides, fungicides, bactericides nematicides, mollusicides or mixtures of several of these preparations, if desired together with further carriers, surfactants or application promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilisers.

A preferred method of applying a compound of the formula I or an agrochemical composition which contains at least one of said compounds, is foliar application. The number of applications and the rate of application depend on the risk of infestation by the corresponding pathogen (type of fungus). However, the compound of formula I can also penetrate the plant through the roots via the soil (systemic action) by impregnating the locus of the plant with a liquid composition, or by applying the compounds in solid form to the soil, e.g. in granular form (soil application). The compounds of formula I may also be applied to seeds (coating) by impregnating the seeds either with a liquid formulation containing a compound of the formula I, or coating them with a solid formulation. In special cases, further types of application are also possible, e.g. selective treatment of the plant stems or buds.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg. a.i./ha, most preferably from 200 g to 600 g a.i./ha.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils, epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Particularly advantageous application promoting adjuvants which are able to reduce substantially the rate of application are also natural (animal or vegetable) or synthetic phospholipids of the series of the cephalins and lecithins, e.g. phosphatidyl ethanolamine, phosphatidyl serine, phosphatidyl choline, sphingomyeline, phosphatidyl inisotol, phosphatidyl glycerol, lysolecithin, plasmologenes or cardiolipin, which can be obtained e.g. from animal or plant cells, in particular from the brain, heart, liver, egg yokes or soya beans. Examples of useful physical forms are phosphatidyl choline mixtures. Examples of synthetic phospholipids are dioctanoylphosphatidyl choline and dipalmitoylphosphatidyl choline.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g., the sodium or calcium salt of lignosulfonic acid, of dodecylsulfate or of a mixture of fatty alcohol sulfates obtained from natural fatty acids.

These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine polypropylene glycol and alkylpolypropylene glycol containing 1 to 10 carbon atoms in the alkyl chain, which adducts contain 20 to 250 ethylene glycol ether groups and 10 or 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethylene ethanol, polyethylene glycol and octylphenoxypolyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", BC Publishing Corp. Ridgewood, N.J., 1981. Helmut Stache "Tensid-Taschenbuch", Carl Hanser Verlag, Munich/Vienna, 1981.

The agrochemical compositions usually contain 0.1 to 99%, preferably 0.1 to 95%, of a compound of the formula I, 99.9 to 1%, preferably 99.8 to 5%, of a solid or liquid adjuvant, and 0 to 25%, preferably 0.1 to 25%, of a surfactant.

Whereas commercial products are preferably formulated as concentrates, the end user will normally employ dilute formulations.

The compositions may also contain further ingredients such as stabilisers, antifoams, viscosity regulators, binders, tackifiers as well as fertilisers or other active ingredients in order to obtain special effects.

Such agrochemical compositions also constitute an object of the present invention.

The invention is illustrated in more detail by the following Examples, without implying any restriction to what is described therein. Parts and percentages are by weight.

PREPARATORY EXAMPLES

Example P1

Preparation of

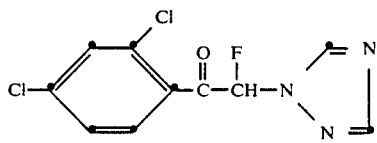

1-(2,4-dichlorophenyl)-2-fluoro-2-(1H-1,2,4-triazol-1-yl)ethanone (a)

Preparation of the intermediate

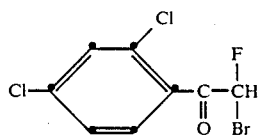

1-(2,4-dichlorophenyl)-2-bromo-2-fluoroethanone

A solution of 16 g of bromine in 100 ml of carbon tetrachloride is added at 40°–45° C. to a solution of 20.7 g of α-fluoro-2,4-dichloroacetophenone in 100 ml of carbon tetrachloride. The brown solution decolorises after approximately 1 hour. The reaction mixture is stirred for 1 hour and then extracted with an aqueous solution of sodium bicarbonate and the extract is concentrated in vacuo by evaporation, affording an oily residue which is then distilled under high vacuum. Yield: 17 g. Boiling point 89°–92° C./0.02 mbar.

(b)

Preparation of the final product 2.9 g of 1,2,4-triazole and 4 ml of diisopropylethylamine are added to 30 ml of acetonitrile. After a weakly exothermic reaction, a pale brown solution forms. With stirring, 5.7 g of 1-(2,4-dichlorophenyl)-2-bromo-2-fluoroethane are added dropwise to this solution at 5°–10° C. and the reaction mixture is kept at this temperature for 1 hour. The reaction mixture is then stirred for 4 hours at room temperature and subsequently concentrated and the residue is partitioned between ice-water and diethyl ether. The ethereal phase is separated, dried over sodium sulfate, filtered and concentrated. The residue is purified by chromatography through a column of silica gel. Yield: 2.4 g. Recrystallisation from diisopropyl ether affords the product which melts at 66°–67° C.

Example P2

Preparation of

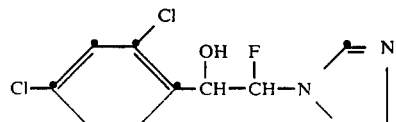

1-(2,4-dichlorophenyl)-2-fluoro-2-(1H-1,2,4-triazol-1-yl)ethanol

With stirring, 0.12 g of sodium borohydride is added at 5°–10° C. to a suspension of 2.4 g of 1-(2,4-dichlorophenyl)-2-fluoro-2-(1H-1,2,4-triazol-1-yl)ethanone in 9.5 ml of methanol and 0.5 ml of water and the resultant mixture is stirred first for 1 hour at 0°–5° C. and then for 2 hours at room temperature, whereupon a clear solution gradually forms. This solution is then poured into ice-water and the mixture is extracted twice with dichloromethane. The combined extracts are dried over sodium sulfate, filtered and concentrated. The residue is distilled under high vacuum, affording the above alkanol as a mixture of diastereoisomers. Boiling point of the crude product: 150°–160° C./0.07 mbar. Crystallisation from diethyl ether/diisopropyl ether affords the purified mixture of diastereoisomers in the form of beige crystals. Melting range 103°–112° C.

Example P3

Preparation and separation of the diastereoisomers of

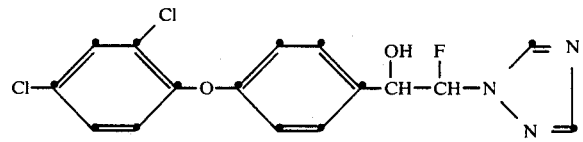

1-[4-(2,4-dichlorophenoxy)phenyl]-2-fluoro-2-(1H-1,2,4-triazol-1-yl)ethanol

With stirring, 0.6 g of sodium borohydride is added at 5°–10° C. to a suspension of 12.1 g of 1-[4-(2,4-dichlorophenoxy)phenyl]-2-fluoro-2-(1H-1,2,4-triazol-1-yl)ethanone in 100 ml of methanol and 2 ml of water and the resultant mixture is stirred further first for 1 hour at 5°–10° C. and then for 2 hours at room temperature, whereupon a clear solution gradually forms. This solution is then poured into ice-water and extracted twice with dichloromethane. The organic phase is separated, washed twice with water, dried over sodium sulfate, filtered and concentrated. The residue is purified by chromatography through a column of silica gel eluted with diethyl ether, affording the following three fractions: The first fraction is concentrated by evaporation and the residue is recrystallised from petroleum ether, affording beige crystals with a melting point of 138°–139° C. Analytic and spectroscopic data show the presence of the pure diastereoisomer A. The second fraction is also concentrated by evaporation and the residue is recrystallised from diethyl ether, affording beige crystals with a melting point of 115°–116° C. Spectroscopic data shows that a mixture of both diastereoisomers A and B (approx. 1:1) is obtained. Similar working up of the third fraction affords the third pure diastereoisomer B with a melting point of 107°–108° C.

Example P4

Preparation of

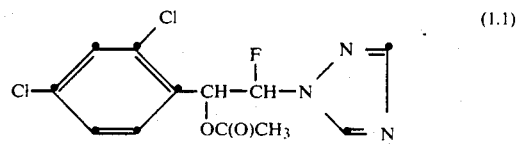

1-(2,4-dichlorophenyl)-1-acetoyl-2-fluoro-2-(1H-1,2,4-triazol-1-yl)ethane (a)

Preparation of the starting material

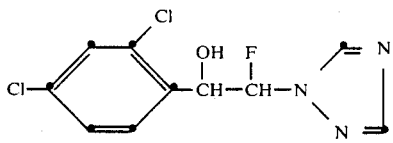

1-(2,4-dichlorophenyl)-2-fluoro-2-(1H-1,2,4-triazol-1-yl)ethanol

With stirring, 0.12 g of sodium borohydride is added at 5°–10° C. to a suspension of 2.4 g of 1-(2,4-dichlorophenyl)-2-fluoro-2-(1H-1,2,4-triazol-1-yl)ethanone in 9.5 ml of methanol and 0.5 ml of water and the resultant mixture is stirred first for 1 hour at 0°–5° C. and then for 2 hours at room temperature, whereupon a clear solution gradually forms. This solution is then poured into ice-water and the mixture is extracted twice with dichloromethane. The combined extracts are dried over sodium sulfate, filtered and concentrated. The residue is distilled under high vacuum, affording the above alkanol as a mixture of diastereoisomers. The boiling point of the crude product is 150°–160° C./0.07 mbar. Crystallisation from diethyl ether/diisopropyl ether affords the purified mixture of diastereoisomers in the form of beige crystals with a melting range of 103°–112° C.

(b)

Preparation of the end product

With efficient stirring, 27.6 g of 1-(2,4-dichlorophenyl)-2-fluoro-2-(1H-1,2,4-triazol-b 1-yl)ethanol are added at −5° C. to a mixture of 250 ml of 2n NaOH solution and 400 ml of diethyl ether. 20 ml of acetyl chloride are then added dropwise at −5° C. and the reaction mixture is stirred at this temperature for 1 hour and then further stirred until it has reached room temperature. The ethereal phase is separated, washed with water until neutral, dried over sodium sulfate, filtered and concentrated, affording 30 g of a pale oil which crystallises from methanol. After recrystallisation from diisopropyl ether/cyclohexanone the product melts at 105°–106° C.

Example P5

Preparation of

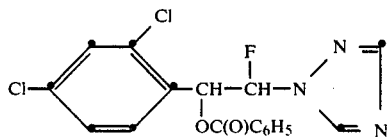 (1.15)

1-(2,4-dichlorophenyl)-1-benzoyl-2-fluoro-2-(1H-1,2,4-triazol-1-yl)ethane

With efficient stirring, a solution of 25 ml of benzoyl chloride in 250 ml of diethyl ether is added dropwise at 0°–5° C. to a mixture of 250 ml of 2n NaOH solution and 27.6 g of 1-(2,4-dichlorophenyl)-2-fluoro-2-(1H-1,2,4-triazol-1-yl)ethanol (prepared in accordance with Example P1a). The reaction mixture is stirred for another 2 hours at 0°–5° C. and then further without cooling until it has reached room temperature. The separated ethereal phase is washed with four 50 ml portions of 0.2n NaOH solution and then with water until neutral, dried over sodium sulfate, filtered and concentrated by evaporation, affording as crude product 40 g of an oil which is purified by flash distillation at 0.07 mbar and 180° C. Recrystallisation from diisopropyl ether affords approx. 26 g of the product which melts at 104°–108° C.

Example P6

Preparation of

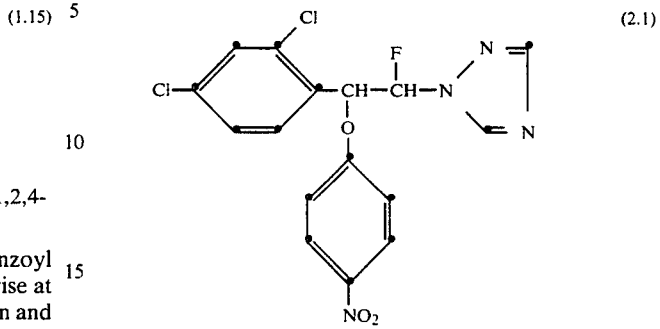 (2.1)

1-(2,4-dichlorophenyl)-1-(4-nitrophenoxy)-2-fluoro-2-(1H-1,2,4-triazol-1-yl)ethane With efficient stirring, 27.6 g of 1-(2,4-dichlorophenyl)-2-fluoro-2-(1H-1,2,4-triazolyl)ethanol (prepared in accordance with Example P1a) were added to a mixture of 250 ml of 2n NaOH solution, 250 ml of diethyl ether and 0.5 g of tetrabutylammonium bromide. 25 ml of 4-nitrofluorobenzene are added at 20° C. to this mixture, which is stirred for another 20 hours at room temperature. The separated ethereal phase is washed with water until neutral, dried over sodium sulfate, filtered and concentrated by evaporation. The crude oily product (35 g) is purified by chromatography through silica gel and melts after recrystallisation from diisopropyl ether/cyclohexanone at 98°–100° C.

The compounds of formula I listed below are prepared in a manner analogous to the procedures described above:

TABLE 1

Compounds of the formula

| Compound | $R_1$ | $R_2$ | $R_3$ | R | Y | Physical data [°C.] |
|---|---|---|---|---|---|---|
| 1.1 | 2-Cl | 4-Cl | H | H | N | m.p. 66–67 |
| 1.2 | 2-Cl | 4-Cl | H | H | CH | b.p. 160/0.07 mbar |
| 1.3 | 2-Cl | 4-Cl | H | $CH_3$ | N | m.p. 64–65 |
| 1.4 | 2-Cl | 4-Cl | H | $CH_3$ | CH | b.p. 160/0.13 mbar |
| 1.5 | 2-Cl | 4-Cl | H | $C_2H_5$ | N | b.p. 150/0.07 mbar |
| 1.6 | 2-Cl | 4-Cl | H | $C_4H_9-n$ | N | |
| 1.7 | 2-Cl | H | H | $C_6H_{13}-n$ | N | |
| 1.8 | 2-Cl | H | H | H | N | m.p. 58–60 |
| 1.9 | H | H | H | H | N | m.p. 85–81 |
| 1.10 | H | H | H | $CH_3$ | N | b.p. 140/0.13 mbar |
| 1.11 | H | H | H | $C_4H_9-n$ | N | b.p. 150/0.12 mbar |
| 1.12 | 2-Cl | 4-Cl | H | $C_3H_7-n$ | N | m.p. 72–73 |
| 1.13 | 2-Cl | 4-Cl | H | $C_2H_5$ | CH | |
| 1.14 | H | 4-F | H | H | N | m.p. 93–95 |
| 1.15 | H | 4-F | H | $C_4H_9-n$ | N | |
| 1.16 | H | 4-F | H | $CH_3$ | N | oil, $n_D^{50}$ 1.544 |
| 1.17 | H | 4-F | H | $C_5H_{11}-n$ | CH | |
| 1.18 | H | 4-Cl | H | H | N | m.p. 128–130 |
| 1.19 | H | 4-Cl | H | $CH_3$ | N | |
| 1.20 | H | 4-Cl | H | $C_2H_5$ | N | |
| 1.21 | H | 4-Cl | H | $C_2H_5$ | CH | |
| 1.22 | H | 4-Cl | H | $C_6H_{13}-n$ | N | |
| 1.23 | 3-Cl | 4-Cl | H | H | N | m.p. 111–114 |
| 1.24 | 3-Cl | 4-Cl | H | $CH_3$ | N | |
| 1.25 | 2-Cl | H | 5-Cl | H | N | m.p. 65–66 |

TABLE 1-continued

Compounds of the formula

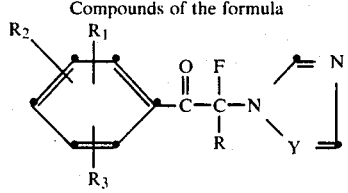

| Compound | R₁ | R₂ | R₃ | R | Y | Physical data [°C.] |
|---|---|---|---|---|---|---|
| 1.26 | 3-Cl | 4-CH₃ | 5-Cl | H | N | |
| 1.27 | 2-CH₃ | 4-CH₃ | H | H | N | m.p. 92-95 |
| 1.28 | H | 4-Br | H | H | N | m.p. 150-152 |
| 1.29 | H | 4-Br | H | CH₃ | N | |
| 1.30 | H | 4-Br | H | CH₃ | CH | |
| 1.31 | H | 4-Br | H | C₂H₅ | N | |
| 1.32 | H | 4-Br | H | C₄H₉—n | CH | |
| 1.33 | H | 4-Br | H | C₆H₁₃—n | N | |
| 1.34 | 2-Cl | 4-F | H | H | N | $n_D^{50}$ 1.532 |
| 1.35 | 2-Cl | 4-F | H | CH₃ | N | |
| 1.36 | 2-Cl | 4-F | H | C₂H₅ | N | |
| 1.37 | H | 4-F | H | H | N | m.p. 65-66 |
| 1.38 | 2-Cl | 4-Br | H | H | N | |
| 1.39 | 2-Cl | 4-Br | H | CH₃ | N | |
| 1.40 | 2-Cl | 4-Br | H | C₂H₅ | N | |
| 1.41 | 2-Cl | 4-Br | H | C₂H₅ | CH | |
| 1.42 | 2-Cl | 4-Br | H | C₄H₉—n | N | |
| 1.43 | 2-Cl | 4-Br | H | C₆H₁₃—n | N | |
| 1.44 | 2-CF₃ | 4-Cl | H | H | N | |
| 1.45 | 2-CF₃ | 4-Cl | H | CH₃ | N | |
| 1.46 | 2-Cl | 4-OCHF₂ | H | H | N | |
| 1.47 | 2-Cl | 4-OCHF₂ | H | CH₃ | N | |
| 1.48 | 2-Cl | 4-OCHF₂ | H | CH₃ | CH | |
| 1.49 | 2-OCHF₂ | 4-Cl | H | H | N | |
| 1.50 | 2-OCHF₂ | 4-Cl | H | H | CH | |
| 1.51 | H | 4-CN | H | H | N | |
| 1.52 | 2-OCH₃ | 4-Cl | H | H | N | |
| 1.53 | 3-OCH₃ | 4-OCH₃ | 5-OCH₃ | H | N | |
| 1.54 | 2-C₂H₅ | 4-Cl | H | H | N | |
| 1.55 | 2-CH₃ | 4-Cl | H | H | N | |
| 1.56 | 2-F | 4-F | H | H | N | m.p. 53-55 |
| 1.57 | 2-Cl | 3-Cl | 4-Cl | H | N | m.p. 111-113 |
| 1.58 | H | 4-OCH₃ | H | H | N | m.p. 99-100 |
| 1.59 | H | 4-OCH₃ | H | CH₃ | N | oil, $n_D^{50}$ 1.583 |
| 1.60 | H | 3-OCH₃ | H | H | N | b.p. 150/0.07 mbar |
| 1.61 | H | 2-OCH₃ | H | H | N | m.p. 98-99 |
| 1.62 | 2-CH₃ | 4-CH₃ | H | C₃H₇—n | N | b.p. 150/0.1 mbar |
| 1.63 | 2-Cl | 3-Cl | H | H | N | m.p. 76-79 |
| 1.64 | 2-C₂H₅ | 4-C₂H₅ | H | H | N | m.p. 45-50 |
| 1.65 | 2-CH₃ | 4-CH₃ | 6-CH₃ | H | N | m.p. 86-88 |
| 1.66 | 2-CH₃ | 4-CH₃ | H | CH₃ | N | |
| 1.67 | 2-CH₃ | 4-CH₃ | H | C₂H₅ | N | |
| 1.68 | 2-CH₃ | 4-CH₃ | H | C₃H₇—n | N | |
| 1.69 | 2-CH₃ | 4-Cl | H | CH₃ | N | |
| 1.70 | 2-CH₃ | 4-Cl | H | C₂H₅ | N | |
| 1.71 | 2-CH₃ | 4-Cl | H | C₃H₇—n | N | |
| 1.72 | 2-Cl | 4-CH₃ | H | H | N | |
| 1.73 | 2-Cl | 4-CH₃ | H | CH₃ | N | |
| 1.74 | 2-Cl | 4-CH₃ | H | C₂H₅ | N | |
| 1.75 | 2-Cl | 4-CH₃ | H | C₃H₇—n | N | |
| 1.76 | 2-Cl | 4-CF₃ | H | H | N | |
| 1.77 | 2-Cl | 4-CF₃ | H | CH₃ | N | |
| 1.78 | 2-Cl | 4-CF₃ | H | C₂H₅ | N | |

TABLE 2

Compounds of the formula

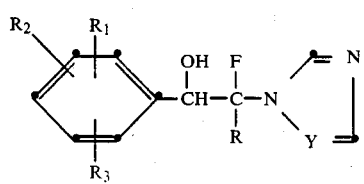

| Compound | R₁ | R₂ | R₃ | R | Y | Physical data [°C.] |
|---|---|---|---|---|---|---|
| 2.1 | 2-Cl | 4-Cl | H | H | N | m.p. 103-112 |

TABLE 2-continued

Compounds of the formula

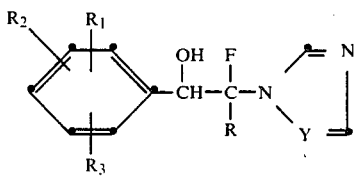

| Compound | R₁ | R₂ | R₃ | R | Y | Physical data [°C.] |
|---|---|---|---|---|---|---|
| 2.2 | 2-Cl | 4-Cl | H | H | CH | |
| 2.3 | 2-Cl | 4-Cl | H | CH₃ | N | m.p. 121-122 |
| 2.4 | 2-Cl | 4-Cl | H | CH₃ | CH | m.p. 109-113 |
| 2.5 | 2-Cl | 4-Cl | H | C₂H₅ | N | m.p. 113-122 |
| 2.6 | 2-Cl | 4-Cl | H | C₄H₉—n | N | |
| 2.7 | 2-Cl | 4-Cl | H | C₆H₁₃—n | N | |
| 2.8 | 2-Cl | H | H | H | N | m.p. 100-103 |
| 2.9 | H | H | H | H | N | b.p. 150/0.07 mbar |
| 2.10 | H | H | H | CH₃ | N | m.p. 110-112 |
| 2.11 | H | H | H | C₄H₉—n | N | m.p. 117-120 |
| 2.12 | 2-Cl | 4-Cl | H | C₃H₇—n | N | m.p. 110-125 |
| 2.13 | 2-Cl | 4-Cl | H | C₂H₅ | CH | m.p. 187-194 |
| 2.14 | H | 4-F | H | H | N | m.p. 78-88 |
| 2.15 | H | 4-F | H | C₄H₉—n | CH | |
| 2.16 | H | 4-F | H | CH₃ | N | m.p. 146-148 |
| 2.17 | H | 4-Cl | H | H | N | m.p. 86-89 |
| 2.18 | H | 4-Cl | H | CH₃ | N | |
| 2.19 | H | 4-Cl | H | C₂H₅ | N | |
| 2.20 | H | 4-Cl | H | C₂H₅ | CH | |
| 2.21 | H | 4-Cl | H | C₆H₁₃—n | N | |
| 2.22 | 3-Cl | 4-Cl | H | H | N | m.p. 88-91 |
| 2.23 | 2-Cl | 3-Cl | H | CH₃ | N | |
| 2.24 | 2-Cl | H | 5-Cl | H | N | m.p. 153-155 |
| 2.25 | 3-Cl | 4-Cl | H | CH₃ | N | |
| 2.26 | 3-Cl | 4-CH₃ | 5-Cl | H | N | |
| 2.27 | 2-CH₃ | 4-CH₃ | H | H | N | m.p. 88-91 |
| 2.28 | H | 4-Br | H | H | N | m.p. 85-95 |
| 2.29 | 2-CH₃ | 4-CH₃ | H | C₃H₇—n | N | m.p. 81-95 |
| 2.30 | 2-Cl | 4-F | H | H | N | m.p. 29-31 |
| 2.31 | 2-Cl | 4-F | H | CH₃ | N | |
| 2.32 | 2-Cl | 4-F | H | C₂H₅ | N | |
| 2.33 | 2-Cl | 4-Br | H | H | N | |
| 2.34 | 2-Cl | 4-Br | H | CH₃ | N | |
| 2.35 | 2-CF₃ | 4-Cl | H | H | N | |
| 2.36 | 2-CF₃ | 4-Cl | H | CH₃ | N | |
| 2.37 | 2-Cl | 4-OCHF₂ | H | H | N | |
| 2.38 | 2-Cl | 4-OCHF₂ | H | CH₃ | N | |
| 2.39 | 2-Cl | 3-Cl | H | H | N | m.p. 122-126 |
| 2.40 | 2-OCHF₂ | 4-Cl | H | H | N | |
| 2.41 | 2-C₂H₅ | 4-C₂H₅ | H | H | N | m.p. 80-90 |
| 2.42 | 2-CH₃ | 4-CH₃ | 6-CH₃ | H | N | $n_D^{60}$ 1.540 |
| 2.43 | 2-CH₃ | 4-CH₃ | H | CH₃ | N | |
| 2.44 | 2-CH₃ | 4-CH₃ | H | C₂H₅ | N | |
| 2.45 | 2-CH₃ | 4-CH₃ | H | C₃H₇—n | N | |
| 2.46 | 2-CH₃ | 4-Cl | H | CH₃ | N | |
| 2.47 | 2-CH₃ | 4-Cl | H | C₂H₅ | N | |
| 2.48 | 2-CH₃ | 4-Cl | H | C₃H₇—n | N | |
| 2.49 | 2-Cl | 4-CH₃ | H | H | N | |
| 2.50 | H | 4-NO₂ | H | H | N | |
| 2.51 | H | 4-CN | H | H | N | |
| 2.52 | 2-OCH₃ | 4-Cl | H | H | N | |
| 2.53 | 3-OCH₃ | 4-OCH₃ | 5-OCH₃ | H | N | |
| 2.54 | 2-C₂H₅ | 4-C₂H₅ | H | H | N | m.p. 80-90 |
| 2.55 | 2-CH₃ | 4-CH₃ | 6-CH₃ | H | N | $n_D^{60}$ 1.540 |
| 2.56 | 2-F | 4-F | H | H | N | m.p. 132-134 |
| 2.57 | 2-Cl | 3-Cl | 4-Cl | H | N | m.p. 120-126 |
| 2.58 | H | 4-OCH₃ | H | H | N | m.p. 99-101 |
| 2.59 | H | 4-OCH₃ | H | CH₃ | N | m.p. 118-120 |
| 2.60 | H | 3-OCH₃ | H | H | N | m.p. 80-82 |
| 2.61 | H | 2-OCH₃ | H | H | N | m.p. 114-116 |
| 2.62 | 2-Cl | 4-CH₃ | H | CH₃ | N | |
| 2.63 | 2-Cl | 4-CH₃ | H | C₂H₅ | N | |
| 2.64 | 2-Cl | 4-CH₃ | H | C₃H₇—n | N | |
| 2.65 | 2-Cl | 4-CF₃ | H | H | N | |
| 2.66 | 2-Cl | 4-CF₃ | H | CH₃ | N | |
| 2.67 | 2-Cl | 4-CF₃ | H | C₂H₅ | N | |

TABLE 3

Compounds of the formula

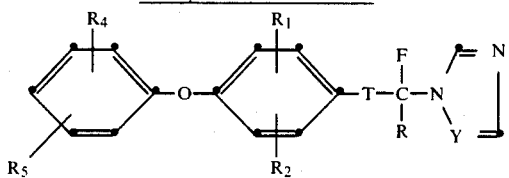

| Compound | $R_1$ | $R_2$ | $R_4$ | $R_5$ | T | R | Y | Physical data [°C.] |
|---|---|---|---|---|---|---|---|---|
| 3.1 | H | H | H | H | —CO— | H | N | |
| 3.2 | H | H | H | H | —CHOH— | H | N | |
| 3.3 | H | H | H | H | —CO— | $CH_3$ | N | |
| 3.4 | H | H | H | H | —CHOH— | $CH_3$ | N | |
| 3.5 | H | H | H | H | —CO— | H | CH | |
| 3.6 | H | H | H | 4-Cl | —CO— | H | N | m.p. 159–160° |
| 3.7 | H | H | H | 4-Cl | —CHOH— | H | N | m.p. 92–94° |
| 3.8 | H | H | H | 4-Cl | —CHOH— | H | CH | |
| 3.9 | H | H | H | 4-Cl | —CHOH— | $CH_3$ | CH | |
| 3.10 | H | H | H | 4-Cl | —CO— | $CH_3$ | N | oil, $n_D^{50}$ 1.586 |
| 3.11 | H | H | H | 4-Cl | —CHOH— | $CH_3$ | N | m.p. 95–99° |
| 3.12 | H | H | 2-Cl | 4-Cl | —CO— | H | N | m.p. 146–147° |
| 3.13 | H | H | 2-Cl | 4-Cl | —CHOH— | H | N | m.p. 138–139°* |
| 3.14 | H | H | 2-Cl | 4-Cl | —CHOH— | H | N | m.p. 107–108°** |
| 3.15 | H | H | 2-Cl | 4-Cl | —CHOH— | H | N | m.p. 115–116°*** |
| 3.16 | H | H | 2-Cl | 4-Cl | —CO— | $CH_3$ | N | $n_D^{50}$ 1.579 |
| 3.17 | H | H | 2-Cl | 4-Cl | —CHOH— | $CH_3$ | N | $n_D^{50}$ 1.562 |
| 3.18 | H | H | 2-Cl | 4-Cl | —CO— | $C_2H_5$ | N | |
| 3.19 | H | H | 2-Cl | 4-Cl | —CHOH— | $C_2H_5$ | N | |
| 3.20 | H | H | 2-Cl | 4-Cl | —CO— | $CH_3$ | CH | |
| 3.21 | 2-Cl | H | H | H | —CO— | H | N | |
| 3.22 | 2-Cl | H | H | H | —CHOH— | H | N | |
| 3.23 | 2-Cl | H | H | H | —CO— | $CH_3$ | N | |
| 3.24 | 2-Cl | H | H | H | —CHOH— | $CH_3$ | N | |
| 3.25 | 2-Cl | H | H | 4-Cl | —CO— | H | N | $n_D^{50}$ 1.596 |
| 3.26 | 2-Cl | H | H | 4-Cl | —CHOH— | H | N | m.p. 143–144 |
| 3.27 | 2-Cl | H | H | 4-Cl | —CO— | $CH_3$ | N | oil, $n_D^{50}$ 1.585 |
| 3.28 | 2-Cl | H | H | 4-Cl | —CHOH— | $CH_3$ | N | m.p. 135–137 |
| 3.29 | 2-$CH_3$ | H | H | 4-Cl | —CO— | H | N | m.p. 59–61 |
| 3.30 | 2-$CH_3$ | H | H | 4-Cl | —CHOH— | H | N | $n_D^{50}$: 1.555 |
| 3.31 | 2-$CH_3$ | H | H | 4-Cl | —CO— | $CH_3$ | N | m.p. 60–62 |
| 3.32 | 2-$CH_3$ | H | H | 4-Cl | —CHOH— | $CH_3$ | N | |
| 3.33 | 2-$CH_3$ | H | H | 4-Cl | —CO— | $C_2H_5$ | N | |
| 3.34 | 2-$CH_3$ | H | H | 4-Cl | —CHOH— | $C_2H_5$ | N | |
| 3.35 | 2-$CH_3$ | H | H | 4-Cl | —CO— | $C_6H_{13}(n)$ | N | |
| 3.36 | 2-$CH_3$ | 3-$CH_3$ | H | 4-Cl | —CO— | H | N | |
| 3.37 | 2-$CH_3$ | 3-$CH_3$ | H | 4-Cl | —CHOH— | H | N | |
| 3.38 | 2-Cl | H | H | 4-F | —CO— | H | N | |
| 3.39 | 2-Cl | H | H | 4-F | —CHOH— | H | N | |
| 3.40 | 2-Cl | H | H | 4-F | —CO— | $C_2H_5$ | N | |
| 3.41 | 2-Cl | H | H | 4-F | —CHOH— | —$C_2H_5$ | N | |
| 3.42 | H | H | H | 4-Cl | —CO— | —$C_2H_5$ | N | |
| 3.43 | H | H | H | 4-Cl | —CHOH— | —$C_2H_5$ | N | |
| 3.44 | 2-Cl | H | H | 4-Cl | —CO— | —$C_2H_5$ | N | |
| 3.45 | 2-Cl | H | H | 4-Cl | —CHOH— | —$C_2H_5$ | N | |
| 3.46 | 2-Cl | H | H | 4-Cl | —CHOH— | $C_2H_5$ | N | m.p. 95–97 |
| 3.47 | 2-$CH_3$ | H | H | 4-Cl | —CHOH— | $C_2H_5$ | N | m.p. 124–126* |
| 3.48 | 2-$CH_3$ | H | H | 4-Cl | —CHOH | $C_2H_5$ | N | m.p. 106–108** |

*diastereoisomer A
**diastereoisomer B
***mixture of diastereoisomers

TABLE 4

Compounds of the formula

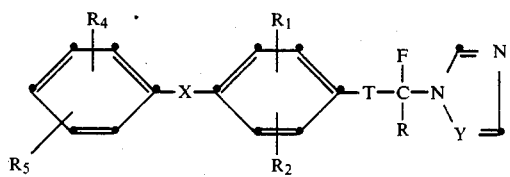

| Compound | $R_1$ | $R_2$ | $R_4$ | $R_5$ | T | R | X | Y | Physical data [°C.] |
|---|---|---|---|---|---|---|---|---|---|
| 4.1 | H | H | H | H | —CO— | H | S | N | |
| 4.2 | H | H | 2-Cl | H | —CHOH— | $CH_3$ | $SO_2$ | N | |

TABLE 4-continued

Compounds of the formula

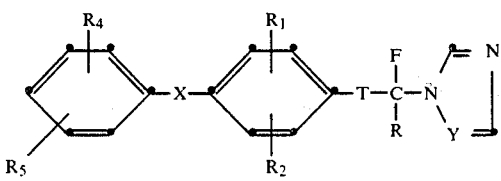

| Compound | R₁ | R₂ | R₄ | R₅ | T | R | X | Y | Physical data [°C.] |
|---|---|---|---|---|---|---|---|---|---|
| 4.3 | 2-Cl | H | H | 4-Cl | —CO— | H | SO₂ | N | |
| 4.4 | 2-Cl | H | H | 4-Cl | —CHOH— | H | SO₂ | N | |
| 4.5 | H | H | H | H | —CO— | H | SO | CH | |
| 4.6 | H | H | 2-Cl | 4-Cl | —CO— | H | S | N | |
| 4.7 | H | H | 2-Cl | 4-Cl | —CHOH— | H | S | N | |
| 4.8 | 2-Cl | H | H | 4-Cl | —CO— | H | S | N | |
| 4.9 | 2-Cl | H | H | 4-Cl | —CHOH | H | S | N | |

TABLE 5

Esters of the formula

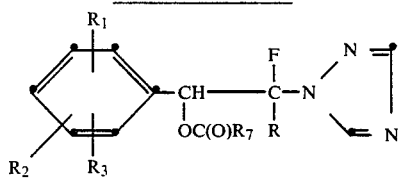

| Compound | R₁, R₂, R₃ | R | R₇ | Physical data [°C.] |
|---|---|---|---|---|
| 5.1 | 2,4-Cl₂ | H | —CH₃ | m.p. 105–106° |
| 5.2 | 2,4-Cl₂ | H | —C₂H₅ | |
| 5.3 | 2,4-Cl₂ | H | —C₃H₇(n) | oil, $n_D^{50}$ 1.531 |
| 5.4 | 2,4-Cl₂ | H | —C₃H₇(i) | |
| 5.5 | 2,4-Cl₂ | H | —C₄H₉(n) | |
| 5.6 | 2,4-Cl₂ | H | —CH₂OCH₃ | |
| 5.7 | 2,4-Cl₂ | H | —CH₂Cl | |
| 5.8 | 2,4-Cl₂ | H | —CF₃ | |
| 5.9 | 2,4-Cl₂ | H | —cyclopropyl | oil, $n_D^{50}$ 1.598*** |
| 5.10 | 2,4-Cl₂ | H | —cyclohexyl | m.p. 140–142°* |
| 5.11 | 2,4-Cl₂ | H | —CH=CH—CH₃ | oil, $n_D^{50}$ 1.601* |
| 5.12 | 2,4-Cl₂ | H | —C≡CH | |
| 5.13 | 2,4-Cl₂ | H | —furyl(2) | m.p. ca. 30°*** |
| 5.14 | 2,4-Cl₂ | H | —tetrahydrofuryl(2) | |
| 5.15 | 2,4-Cl₂ | H | —C₆H₅ | m.p. 104–109° |
| 5.16 | 2,4-Cl₂ | H | —C₆H₄Cl(4) | m.p. 131–133° |
| 5.17 | 2,4-Cl₂ | H | —C₆H₄Cl(2) | m.p. 116–117°* |
| 5.18 | 2,4-Cl₂ | H | —C₆H₃Cl₂(2,4) | m.p. 85–87° |
| 5.19 | 2,4-Cl₂ | H | —C₆H₃Cl₂(2,6) | |
| 5.20 | 2,4-Cl₂ | H | —C₆H₄CH₃(4) | m.p. 155–156° |
| 5.21 | 2,4-Cl₂ | H | —C₆H₄CF₃(2) | |
| 5.22 | 2,4-Cl₂ | H | —C₆H₄OCH₃(4) | m.p. 137–139°* |
| 5.23 | 2,4-Cl₂ | H | —C₆H₄OCHF₂(4) | |
| 5.24 | 2,4-Cl₂ | H | —CH₂C₆H₅ | oil, $n_D^{50}$ 1.587* |
| 5.25 | 2,4-Cl₂ | H | —CH₂C₆H₄Cl(4) | |
| 5.26 | 2,4-Cl₂ | H | —CH₂C₆H₄Cl(2) | |
| 5.27 | 2,4-Cl₂ | H | —CH₂Ch₆H₄NO₂(4) | |
| 5.28 | 2,4-Cl₂ | —CH₃ | —CH₃ | |
| 5.29 | 2,4-Cl₂ | —CH₃ | —C₂H₅ | |
| 5.30 | 2,4-Cl₂ | —CH₃ | —CH₂OCH₃ | |
| 5.31 | 2,4-Cl₂ | —CH₃ | —C₆H₅ | |
| 5.32 | 2,4-Cl₂ | —CH₃ | —furyl(2) | oil, $n_D^{50}$ 1.731 |
| 5.33 | 2,4-Cl₂ | —CH₃ | —tetrahydrofuryl(2) | |
| 5.34 | 2,4-Cl₂ | —CH₃ | —C₆H₄Cl(4) | |
| 5.35 | 2,4-Cl₂ | —C₂H₅ | —CH₃ | |
| 5.36 | 2,4-Cl₂ | —C₂H₅ | —C₂H₅ | |
| 5.37 | 2,4-Cl₂ | —C₂H₅ | —C₆H₁₃(n) | |
| 5.38 | 2,4-Cl₂ | —C₂H₅ | —CH₂CH₂OCH₃ | |
| 5.39 | 2,4-Cl₂ | —C₂H₅ | —C₆H₅ | m.p. 88–90° |
| 5.40 | 2-Cl, 4-F | —H | —CH₃ | |
| 5.41 | 2-Cl, 4-F | —H | —C₂H₅ | |
| 5.42 | 2-Cl, 4-F | —H | —CH₂OCH₃ | |
| 5.43 | 2-Cl, 4-F | —H | —C₆H₅ | |
| 5.44 | 2-Cl, 4-F | —CH₃ | —CH₃ | |
| 5.45 | 2-Cl, 4-F | —CH₃ | —CH₂Cl | |

TABLE 5-continued

Esters of the formula

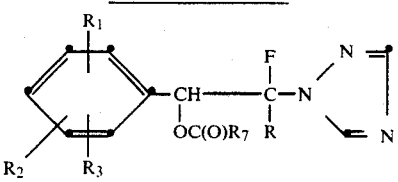

| Compound | $R_1, R_2, R_3$ | R | $R_7$ | Physical data [°C.] |
|---|---|---|---|---|
| 5.46 | 2-Cl, 4-F | —$CH_3$ | —$C_6H_5$ | |
| 5.47 | 2-Cl, 4-Br | —H | —$CH_3$ | |
| 5.48 | 2-Cl, 4-Br | —H | —$C_5H_{11}(n)$ | |
| 5.49 | 2-$CF_3$, 4-Cl | —H | —$CH_2OCH_3$ | |
| 5.50 | 2-$CF_3$, 4-Cl | —H | —$CH_6H_5$ | |
| 5.51 | 2-$CF_3$, 4-Cl | —$CH_3$ | —$CH_3$ | |
| 5.52 | 2-$CF_3$, 4-Cl | —$CH_3$ | —cyclopentyl | |
| 5.53 | 2-Cl, 4-$OCHF_2$ | —H | —$CH_3$ | |
| 5.54 | 2-Cl, 4-$OCHF_2$ | H | $CH_2OCH_3$ | |
| 5.55 | 2-Cl, 4-$OCHF_2$ | H | $C_6H_5$ | |
| 5.56 | 2-Cl, 4-$OCHF_2$ | $CH_3$ | $C_2H_5$ | |
| 5.57 | 2-$CH_3$, 4-Cl | H | $C_6H_5$ | |
| 5.58 | 2-$CH_3$, 4-Cl | H | $CH_3$ | |
| 5.59 | 2,3-$Cl_2$ | H | $CH_3$ | |
| 5.60 | 2,3-$Cl_2$ | H | $CH_2OCH_3$ | |
| 5.61 | 2,4,6-$(CH_3)_3$ | H | $CH_3$ | |
| 5.62 | 2,4,6-$(CH_3)_3$ | H | $C_6H_5$ | m.p. 161–164° |
| 5.63 | 2,4-$Cl_2$ | H | $C_6H_3Cl_2(3,4)$ | |
| 5.64 | 2,4-$Cl_2$ | H | cyclopropyl | m.p. 115–117°** |
| 5.65 | 2,4-$Cl_2$ | H | $C_6H_4Cl(2)$ | oil, $n_D^{50}$ 1.597*** |
| 5.66 | 2,4-$Cl_2$ | H | 2-furyl | m.p. 156–158°* |
| 5.67 | 2,4-$Cl_2$ | H | 2-furyl | m.p. 101–103°*** |
| 5.68 | 2,4-$Cl_2$ | H | $C_6H_4OCH_3(4)$ | m.p. 141–143°*** |
| 5.69 | 2,4-$Cl_2$ | H | CHad,4 CH—$CH_3$ | m.p. 80–82°** |
| 5.70 | 2,4-$Cl_2$ | H | $C_6H_4F(4)$ | m.p. 130–132°* |
| 5.71 | 2,4-$Cl_2$ | H | $C_6H_4(4)$ | m.p. 90–92°** |
| 5.72 | 2,4-$Cl_2$ | H | cyclohexyl | oil, $n_D^{50}$ 1.630** |
| 5.73 | 2,4-$Cl_2$ | H | $C_6H_4CF_3(4)$ | m.p. 118–119°* |
| 5.74 | 2,4-$Cl_2$ | H | $C_6H_4CF_3(4)$ | m.p. 85–87°*** |
| 5.75 | 2,4-$Cl_2$ | H | $CH_2C_6H_5$ | m.p. 88–90°** |
| 5.76 | 2,4-$Cl_2$ | $CH_3$ | $C_6H_3Cl_2(2,4)$ | oil, $n_D^{50}$ 1.888 |
| 5.77 | 2,4-$Cl_2$ | $CH_3$ | $C_6H_4F(4)$ | oil, $n_D^{50}$ 1.908 |
| 5.78 | 2,4-$Cl_2$ | $CH_3$ | $C_6H_4OCH_3(4)$ | oil, $n_D^{50}$ 1.899** |
| 5.79 | 2,4-$Cl_2$ | $CH_3$ | $C_6H_4OCH_3(4)$ | m.p. 120–122°*** |
| 5.80 | 2,4-$Cl_2$ | H | $CH(C_2H_5)CH_2CH_3$ | m.p. 124–126° |
| 5.81 | 2,4-$Cl_2$ | H | $CH(C_2H_5)CH_2CH$ | oil, $n_D^{50}$ 1.835** |
| 5.82 | 2,4-$Cl_2$ | $CH_3$ | $C_6H_4F(4)$ | oil, $n_D^{50}$ 1.794 |
| 5.83 | 2,4-$Cl_2$ | H | $C_6H_4Cl(4)$ | m.p. 140–142°** |
| 5.84 | 2,4-$Cl_2$ | $CH_3$ | $C_6H_4F(4)$ | m.p. 88–90° |
| 5.85 | 2,4-$Cl_2$ | $CH_3$ | $C_6H_3Cl_2(2,4)$ | m.p. 120–122°* |
| 5.86 | 2,4-$Cl_2$ | $CH_3$ | $C_6H_3Cl_2(2,4)$ | m.p. 102–104°*** |
| 5.87 | 2,4-$Cl_2$ | $C_2H_5$ | $C_6H_3Cl_2(2,4)$ | oil, $n_D^{50}$ 1.877 |
| 5.88 | 2,4-$(CH_3)_2$ | H | $C_6H_5$ | |
| 5.89 | 2,4-$(CH_3)_2$ | H | $C_6H_4F(4)$ | |
| 5.90 | 2,4-$(CH_3)_2$ | H | $C_6H_4Cl(4)$ | |
| 5.91 | 2,4-$(CH_3)_2$ | H | $CH_3$ | |
| 5.92 | 2,4-$(CH_3)_2$ | H | $CH=CHCH_3$ | |
| 5.93 | 2,4-$(Ch_3)_2$ | $CH_3$ | $C_6H_5$ | |
| 5.94 | 2,4-$(CH_3)_2$ | $CH_3$ | $C_6H_4CF_3(4)$ | |
| 5.95 | 2,4-$(CH_3)_2$ | $CH_3$ | 2-furyl | |
| 5.96 | 2,4-$(CH_3)_2$ | $CH_3$ | $CH=CHCH_3$ | |
| 5.97 | 2,4-$(CH_3)_2$ | $C_2H_5$ | $CH_3$ | |
| 5.98 | 2,4-$(CH_3)_2$ | $C_2H_5$ | $C_6H_5$ | |
| 5.99 | 2,4-$(CH_3)_2$ | $C_2H_5$ | $C_6H_4F(4)$ | |
| 5.100 | 2,4-$(CH_3)_2$ | $C_3H_7$—n | $C_6H_5$ | |
| 5.101 | 2,4-$(CH_3)_2$ | $C_3H_7$—n | 2-furyl | |

*diastereoisomer A
**diastereoisomer B
***mixture of diastereoisomers

TABLE 6

Ethers of the formula

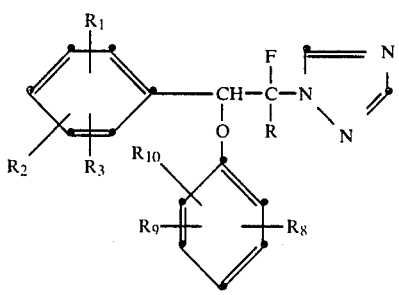

| Compound | $R_1, R_2, R_3$ | R | $R_8, R_9, R_{10}$ | Physical data [°C.] |
|---|---|---|---|---|
| 6.1 | 2,4-$Cl_2$ | —H | 4-$NO_2$ | m.p. 98–100° |
| 6.2 | 2,4-$Cl_2$ | —H | H | |
| 6.3 | 2,4-$Cl_2$ | —H | 4-$NH_2$ | m.p. 142–144° |
| 6.4 | 2,4-$Cl_2$ | —H | 4-Cl | b.p. 160°/0.05 mbar |
| 6.5 | 2,4-$Cl_2$ | —H | 4-$NHCOCH_3$ | m.p. 168–171° |
| 6.6 | 2,4-$Cl_2$ | —H | 3-$COOCH_3$, 4-$NO_2$ | |
| 6.7 | 2,4-$Cl_2$ | —H | 2-$NO_2$, 4-$COOCH_3$ | |
| 6.8 | 2,4-$Cl_2$ | —H | 2-$NO_2$, 4-$CF_3$ | |
| 6.9 | 2,4-$Cl_2$ | —H | 2-$NO_2$, 4-$OCH_3$ | m.p. 98–100° |
| 6.10 | 2,4-$Cl_2$ | —H | 2,6-$(NO_2)_2$, 4-CN | |
| 6.11 | 2,4-$Cl_2$ | —H | 2,6-$(NO_2)_2$, 4-$COOCH_3$ | |
| 6.12 | 2,4-$Cl_2$ | —H | 2,6-$(NO_2)_2$, 4-$CF_3$ | |
| 6.13 | 2,4-$Cl_2$ | —H | 2,4-$(NO_2)_2$ | |
| 6.14 | 2,4-$Cl_2$ | —H | 2,4-$(NO_2)_2$, 6-$CF_3$ | |
| 6.15 | 2,4-$Cl_2$ | —$CH_3$ | 4-$NO_2$ | |
| 6.16 | 2,4-$Cl_2$ | —$CH_3$ | 2,4-$(NO_2)_2$ | |
| 6.17 | 2,4-$Cl_2$ | —$CH_3$ | 2-$NO_2$, 4-$CF_3$ | |
| 6.18 | 2,4-$Cl_2$ | —$CH_3$ | 2,6-$(NO_2)_2$, 4-CN | |
| 6.19 | 2,4-$Cl_2$ | —$C_2H_5$ | 4-$NO_2$ | resin, $n_D^{50}$ 1.599 |
| 6.20 | 2,4-$Cl_2$ | —$C_2H_5$ | 2,4-$(NO_2)_2$, 6-$CF_3$ | |
| 6.21 | 2,4-$Cl_2$ | —$C_2H_5$ | 2,4-$(NO_2)_2$ | |
| 6.22 | 4-Cl | —H | 4-$NO_2$ | |
| 6.23 | 4-Cl | —$CH_3$ | 3-$COOCH_3$, 4-$NO_2$ | |
| 6.24 | 4-Cl | —$CH_3$ | 2-$NO_2$, 4-$CF_3$ | |
| 6.25 | 2-$CH_3$, 4-Cl | —H | 4-$NO_2$ | |
| 6.26 | 2-$CH_3$, 4-Cl | —H | 4-$NO_2$ | |
| 6.27 | 2-$CF_3$, 4-Cl | —H | 4-$NO_2$ | |
| 6.28 | 2-$CF_3$, 4-Cl | —H | 2,6-$(NO_2)_2$, 4-$COOCH_3$ | |
| 6.29 | 2-$CF_3$, 4-Cl | —H | 2-$NO_2$, 4-$CF_3$ | |
| 6.30 | 2-$CF_3$, 4-Cl | —$CH_3$ | 2-$NO_2$, 4-$CF_3$ | |
| 6.31 | 2-Cl, 4-Br | —H | 4-$NO_2$ | |
| 6.32 | 2-Cl, 4-Br | —$CH_3$ | 4-$NO_2$ | |
| 6.33 | 2-Cl, 4-$OCHF_2$ | —H | 4-$NO_2$ | |
| 6.34 | 2,4-$Cl_2$ | H | 4-$NO_2$ | m.p. 102–105° * |
| 6.35 | 2,4-$Cl_2$ | H | 4-$NHCOCH_3$ | m.p. 191–194° * |
| 6.36 | 2,4-$Cl_2$ | H | 4-$NH_2$ | m.p. 75–77° ** |
| 6.37 | 2,4-$(CH_3)_2$ | H | 4-$NO_2$ | |
| 6.38 | 2,4-$(CH_3)_2$ | H | 4-$NH_2$ | * |
| 6.39 | 2,4-$(CH_3)_2$ | H | 4-$NHCOCH_3$ | ** |
| 6.40 | 2,4-$(CH_3)_2$ | $CH_3$ | 4-$NO_2$ | |
| 6.41 | 2,4-$(CH_3)_2$ | $C_2H_5$ | 4-$NO_2$ | |
| 6.42 | 2,4-$(CH_3)_2$ | $C_3H_7$—n | 4-$NO_2$ | |

FORMULATION EXAMPLES

Formulation Examples for liquid active ingredients of the formula I (throughout, percentages are by weight)

| F1. Emulsifiable concentrates | (a) | (b) | (c) |
|---|---|---|---|
| a compound of tables | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |

-continued

| F1. Emulsifiable concentrates | (a) | (b) | (c) |
|---|---|---|---|
| xylene mixture | 65% | 25% | 20% |

Emulsions of any required concentration can be produced from such concentrates by dilution with water.

| F2. Solutions | (a) | (b) | (c) | (d) |
|---|---|---|---|---|
| a compound of tables | 80% | 10% | 5% | 95% |
| ethylene glycol monomethyl ether | 20% | — | — | — |
| polyethylene glycol mol. wt. 400 | — | 70% | — | — |
| N—methyl-2-pyrrolidone | — | 20% | — | — |

-continued

| F2. Solutions | (a) | (b) | (c) | (d) |
|---|---|---|---|---|
| epoxidised coconut oil | — | — | 1% | 5% |
| petroleum distillate (boiling range 160–190°) | — | — | 94% | — |

These solutions are suitable for application in the form of microdrops.

| F3. Granulates | (a) | (b) |
|---|---|---|
| a compound of tables | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| F4. Dusts | (a) | (b) |
|---|---|---|
| a compound of tables | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Formulation examples for solid active ingredients of the formula I (throughout, percentages are by weight)

| F5. Wettable powders | (a) | (b) | (c) |
|---|---|---|---|
| a compound of tables | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixtures is thoroughly ground in a suitable mill, affording wettable powders which can be diluted with water to give suspensions of the desired concentration.

| F6. Emulsifiable concentrate | |
|---|---|
| a compound of tables | 10% |
| octylphenol polyethlene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| F7. Dusts | (a) | (b) |
|---|---|---|
| a compound of tables | 5% | 8% |
| talcum | 95% | — |
| kaolin | — | 92% |

Ready-for-use dusts are obtained by mixing the active ingredient with the carriers, and grinding the mixture in a suitable mill.

| F8. Extruder granulate | |
|---|---|
| a compound of tables | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| F9. Coated granulate | |
|---|---|
| a compound of tables | 3% |
| polyethylene glycol mol. wt. 200 | 3% |
| kaolin | 94% |

The finely ground active ingredient is uniformly applied, in a mixer, to the kaolin moistened with polyethylene glycol. Non-dusty coated granulates are obtained in this manner.

| F10. Suspension concentrate | |
|---|---|
| a compound of tables | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

BIOLOGICAL EXAMPLES

In the following Example B1 compounds A and B of the prior art were also tested for comparison purposes:

| DE 2 431 407 | Structurally closest comparable compounds of formula I |
|---|---|
| 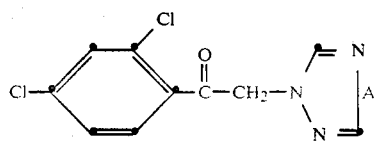 | 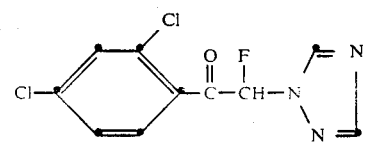 |

| DE 2 431 407 | Structurally closest comparable compounds of formula I |
|---|---|
| (compound 12) | (compound 1.1) |
| (compound 5) | (compound 2.1) |

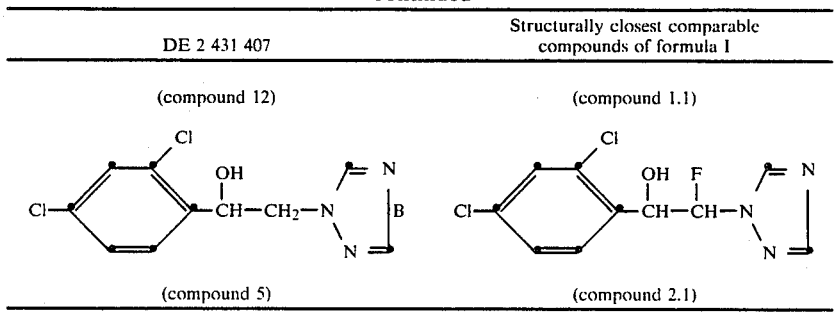

EXAMPLE B1

Action against *Piricularia oryzae* on rice (a)

Residual protective action

After a cultivation period of two weeks, rice plants were sprayed with a spray mixture prepared from a wettable powder formation of the test compound (0.02%). After 48 hours the treated plants were infected with a conidia suspension of the fungus. Evaluation of fungus attack was made after incubation for 5 days at 95-100% relative humidity and about 24° C.

(b)

Systemic action

A spray mixture prepared from a wettable powder formulation of the test compound (0.006%, based on the volume of the soil) was poured onto two-week-old rice plants. The pots were then filled with water until the lowermost stem parts of the rice plants were standing in water. After 96 hours the treated plants were infected with a conidia suspension of the fungus. Evaluation of fungus attack was made after incubation for 5 days at 95-100% relative humidity and about 24° C.

Fungus attack was 100% on untreated and infected control plants in both tests a and b. Fungus attack was reduced to 0-5% on rice plants treated with compounds from Tables 1 to 6, e.g. with one of the compounds 1.1-1.5, 1.9-1.12, 1.14, 1.18, 1.23, 1.25, 1.28, 1.34, 1.37, 1.56-1.59, 1.62-1.65, 2.1, 2.3, 2.5, 2.9-2.14, 2.17, 2.22, 2.24, 2.28, 2.29, 2.30, 2.41, 2.42, 2.56, 3.6, 3.7, 3.12-3.17, 3.25-3.28, 3.30, 3.46, 3.48, 5.1, 5.15-5.18, 5.20, 5.22, 5.32, 5.64-5.69, 5.70-5.78, 5.80-5.87, 6.1, 6.4, 6.5 and 6.34. In particular compounds 1.1, 1.3, 1.4, 1.5, 2.1, 2.3, 2.4 and 2.5 inhibited fungus attack completely (0% attack). In contradistinction thereto, compounds A and B of the prior art did not inhibit Piricularia attack at all at the low test concentrations. As with the untreated controls, attack was 100% on plants treated with compounds A and B.

EXAMPLE B2

Action against *Puccinia graminis* on wheat (a)

Residual-protective action

Wheat plants were sprayed 6 days after sowing with a spray mixture prepared from a wettable powder formulation of the test compound (0.02%). After 24 hours the treated plants were infected with a uredospore suspension of the fungus. The infected plants were incubated for 48 hours at 95-100% relative humidity and about 20° C. and then stood in a greenhouse at about 22° C. Evaluation of rust pustule development was made 12 days after infection.

(b)

Systemic action

A spray mixture prepared from a wettable powder formulation of the test compound (0.006%, based on the volume of the soil) was poured onto wheat plants 5 days after sowing. After 48 hours the treated plants were infected with a uredospore suspension of the fungus. The plants were then incubated for 48 hours at 95-100% relative humidity and about 20° C. and then stood in a greenhouse at about 22° C. Evaluation of rust pustule development was made 12 days after infection.

Compounds from the Tables were very effective against Puccinia fungi. Puccinia attack was 100% on untreated and infected plants. Compounds 1.1-1.5, 1.8-1.10, 1.12, 1.14, 1.18, 1.23, 1.28, 1.34, 1.56, 1.58, 1.61, 1.64, 1.65, 2.1-2.5, 2.8-2.14, 2.16, 2.17, 2.24, 2.28-2.30, 2.39, 2.41, 2.42, 2.54, 2.56, 2.58, 3.6, 3.12, 3.14, 3.15, 3.16, 3.25, 3.26, 3.29-3.31, 3.46, 5.1, 5.3, 5.13, 5.15, 5.20, 5.65-5.76, 5.80-5.86, 6.5, 6.9 and others inhibited Puccinia attack almost completely (0-5% attack).

EXAMPLE B3

Action against *Erysiphe graminis* on barley (a)

Residual protective action

Barley plants about 8 cm in height were sprayed with a spray mixture prepared from a wettable powder formulation of the test compound (0.02%). The treated plants were dusted with the conidia of the fungus after 24 hours. The infected barley plants were then stood in a greenhouse at about 22° C. Evaluation of fungus attack was made after 10 days.

(b)

Systemic action

A spray mixture prepared from a wettable powder formulation of the test compound (0.006%, based on the volume of the soil) was poured onto barley plants about 8 cm in height. Care was taken that the spray mixture did not come in contact with the parts of the plants above the soil. The treated plants were dusted 72 hours later with a conidia suspension of the fungus. The infected barley plants were then stood in a greenhouse at about 22° C. Evaluation of fungus attack was made after 10 days.

Compounds of formula I were very effective against Erysiphe fungi. Erysiphe attack was 100% on untreated and infected control plants. Compounds 1.1–1.5, 1.8–1.12, 1.14, 1.16, 1.18, 1.23, 1.25, 1.27, 1.34, 1.37, 1.56–1.65, 2.1, 2.3–2.5, 2.8–2.14, 2.17, 2.27–2.30, 2.39, 2.41, 2.42, 2.54, 2.59, 2.61, 3.6, 3.7, 3.10, 3.11, 3.12, 3.14, 3.15, 3.17, 3.26, 3.27, 3.28, 3.30, 3.46, 5.1, 5.3, 5.9, 5.11, 5.13, 5.15, 5.17, 5.18, 5.20, 5.22, 5.62, 5.64–5.87, 6.1, 6.3, 6.5, 6.19, 6.34, 6.35 and other compounds from the Tables inhibited fungus attack on barley to 0–5%. In particular compounds 1.1 and 2.1 effected complete inhibition (0% attack).

What is claimed is:

1. A compound of formula I

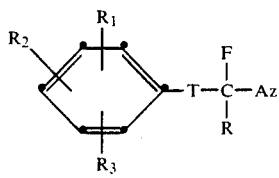

wherein

Az is 1H-1,2,4-triazol-1-yl, 4H-1,2,4-triazol-4-yl or 1H-imidazol-1-yl;

T is —CH(OH)— or one of the groups

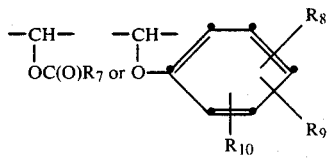

wherein $R_7$ is $C_1$–$C_6$alkyl which is unsubstituted or substituted by $C_1$–$C_3$alkoxy, halogen or cyano, or is $C_3$–$C_6$alkenyl, $C_3$–$C_6$alkynyl, $C_3$–$C_6$cycloalkyl, 2-furyl, 2-tetrahydrofuryl, or is phenyl or benzyl, each unsubstituted or substituted by halogen, nitro, $C_1$–$C_3$alkyl, $C_1$–$C_3$alkoxy, $C_1$–$C_3$haloalkyl or $C_1$–$C_3$haloalkoxy;

$R_8$, $R_9$ and $R_{10}$ are each independently hydrogen, nitro, halogen, cyano, $C_1$–$C_3$alkyl, $C_1$–$C_3$alkoxy, $C_1$–$C_3$haloalkoxy, —COO($C_1$–$C_3$alkyl), $NH_2$ or $NHCOCH_3$;

R is hydrogen or $C_1$–$C_6$alkyl;

$R_1$ and $R_2$ are each independently hydrogen, halogen, $C_1$–$C_6$alkyl, $C_1$–$C_6$alkoxy, $C_1$–$C_6$haloalkyl, $C_1$–$C_6$haloalkoxy, nitro or cyano; and $R_3$ is hydrogen, halogen, $C_1$–$C_6$alkyl, $C_1$–$C_6$alkoxy, $C_1$–$C_6$haloalkyl, $C_1$–$C_6$haloalkoxy, nitro, cyano or the group

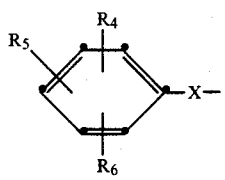

wherein

X is O, S, SO or $SO_2$;

$R_4$, $R_5$ and $R_6$ are each independently hydrogen, halogen, cyano, nitro, $C_1$–$C_6$alkyl, $C_1$–$C_6$alkoxy, $C_1$–$C_6$haloalkyl or $C_1$–$C_6$haloalkoxy; or an acid addition salt or metal complex thereof.

2. A compound according to claim 1, wherein

Az is 1H-1,2,4-triazol-1-yl, 4H-1,2,4-triazol-4-yl or 1H-imidazol-1-yl;

T is —CH(OH)—;

R is hydrogen or $C_1$–$C_6$alkyl;

$R_1$ and $R_2$ are each independently hydrogen, halogen, $C_1$–$C_6$alkyl, $C_1$–$C_6$alkoxy, $C_1$–$C_6$haloalkyl, $C_1$–$C_6$haloalkoxy, nitro or cyano; and $R_3$ is hydrogen, halogen, $C_1$–$C_6$alkyl, $C_1$–$C_6$alkoxy, $C_1$–$C_6$haloalkyl, $C_1$–$C_6$haloalkoxy, nitro, cyano or the group

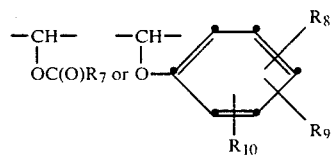

wherein

X is O, S, SO or $SO_2$;

$R_4$, $R_5$ and $R_6$ are each independently hydrogen, halogen, cyano, nitro, $C_1$–$C_6$alkyl, $C_1$–$C_6$alkoxy, $C_1$–$C_6$haloalkyl or $C_1$–$C_6$haloalkoxy; or an acid addition salt or metal complex thereof.

3. A compound according to claim 1, wherein

Az is 1H-1,2,4-triazol-1-yl, 4H-1,2,4-triazol-4-yl or 1H-imidazol-1-yl;

T is one of the groups

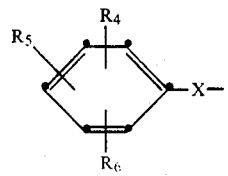

wherein $R_7$ is $C_1$–$C_6$alkyl which is unsubstituted or substituted by $C_1$–$C_3$alkoxy, halogen or cyano, or is $C_3$–$C_6$alkenyl, $C_3$–$C_6$alkynyl, $C_3$–$C_6$cycloalkyl, 2-furyl, 2-tetrahydrofuryl, or is phenyl or benzyl, each unsubstituted or substituted by halogen, nitro, $C_1$–$C_3$alkyl, $C_1$–$C_3$alkoxy, $C_1$–$C_3$haloalkyl or $C_1$–$C_3$haloalkoxy;

$R_8$, $R_9$ and $R_{10}$ are each independently hydrogen, nitro, halogen, cyano, $C_1$–$C_3$alkyl, $C_1$–$C_3$alkoxy, $C_1$–$C_3$haloalkoxy, —COO($C_1$–$C_3$alkyl), $NH_2$ or $NHCOCH_3$;

R is hydrogen or $C_1$–$C_6$alkyl;

$R_1$ and $R_2$ are each independently hydrogen, halogen, $C_1$–$C_6$alkyl, $C_1$–$C_6$alkoxy, $C_1$–$C_6$haloalkyl, $C_1$–$C_6$haloalkoxy, nitro or cyano; and $R_3$ is hydrogen, halogen, $C_1$–$C_6$alkyl, $C_1$–$C_6$alkoxy, $C_1$–$C_6$haloalkyl, $C_1$–$C_6$haloalkoxy, nitro, cyano or the group

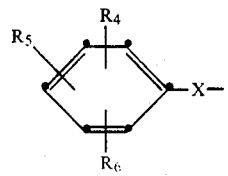

wherein

X is O, S, SO or $SO_2$;

$R_4$, $R_5$ and $R_6$ are each independently hydrogen, halogen, cyano, nitro, $C_1$–$C_6$alkyl, $C_1$–$C_6$alkoxy, $C_1$–$C_6$haloalkyl or $C_1$–$C_6$haloalkoxy; or an acid addition salt or metal complex thereof.

4. A compound according to claim 2, wherein T is —CH(OH)—; Az is 1H-1,2,4-triazol-1-yl; R is hydrogen or $C_1$–$C_4$alkyl; $R_1$ is in ortho-position and $R_2$ is in para-position and each is independently fluorine, chlorine, bromine, methyl, methoxy, $CF_3$, $OCHF_2$, $OCF_3$, nitro or cyano; and $R_3$ is hydrogen; or an acid addition salt or metal complex thereof.

5. A compound according to claim 2, wherein T is —CH(OH)—; Az is 1H-1,2,4-triazol-1-yl; R is hydrogen or $C_1$–$C_4$alkyl; $R_3$ is the group

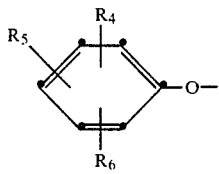

wherein $R_1$, $R_2$, $R_4$, $R_5$ and $R_6$ are each independently hydrogen, fluorine, chlorine, bromine, methyl, methoxy, $CF_3$, $OCF_3$, $OCHF_2$, cyano or nitro; or an acid addition salt or metal complex thereof.

6. A compound according to claim 3 selected from the group consisting of
1-(2,4-dichlorophenyl)-1-acetyloxy-2-fluoro-2-(1H-1,2,4-triazol-1-yl)ethane, (5.1),
1-(2,4-dichlorophenyl)-1-benzoyloxy-2-fluoro-2-(1H-1,2,4-triazol-1-1,2,4-triazol-1-yl)ethane, (5.15),
1-(2,4-dichlorophenyl)-1-(4-nitrophenoxy)-2-fluoro-2-(1H-1,2,4-triazol-1-yl)ethane (6.1).

7. A compound according to claim 1 selected from the group consisting of:
1-(2,4-dichlorophenyl)-2-fluoro-2-(1H-1,2,4-triazol-1-yl)ethan-1-ol;
1-(2,4-dichlorophenyl)-2-fluoro-2-(1H-1,2,4-triazol-1-yl)propan-1-ol;
1-(2,4-dichlorophenyl)-2-fluoro-2-(1H-imidazol-1-yl)propan-1-ol;
1-(2,4-dichlorophenyl)-2-fluoro-2-(1H-1,2,4-triazol-1-yl)butan-1-ol;
1-(phenyl)-2-fluoro-2-(1H-1,2,4-triazol-1-yl)ethan-1-ol;
1-(phenyl)-2-fluoro-2-(1H-1,2,4-triazol-1-yl)propan-1-ol;
1-(phenyl)-2-fluoro-2-(1H-1,2,4-triazol-1-yl)hexan-1-ol;
1-(2,4-dichlorophenyl)-2-fluoro-2-(1H-1,2,4-triazol-1-yl)pentan-1-ol;
1-(2,4-dichlorophenyl)-2-fluoro-2-(1H-imidazol-1yl)butan-1-ol;
1-(4-fluorophenyl)-2-fluoro-2-(1H-1,2,4-triazol-1-yl)ethan-1-ol;
1-(4-chlorophenyl)-2-fluoro-2-(1H-1,2,4-triazol-1-yl)ethan-1-ol;
1-(3,4-dichlorophenyl)-2-fluoro-2-(1H-1,2,4-triazol-1-yl)ethan-1-ol;
1-(2,5-dichlorophenyl)-2-fluoro-2-(1H-1,2,4-triazol-1-yl)ethan-1-ol;
1-(2,4-dimethylphenyl)-2-fluoro-2-(1H-1,2,4-triazol-1-yl)ethan-1-ol;
1-(4-bromophenyl)-2-fluoro-2-(1H-1,2,4-triazol-1-yl)ethan-1-ol;
1-(2,4-difluorophenyl)-2-fluoro-2-(1H-1,2,4-triazol-1-yl)ethan-1-ol;
1-(2,3,4-trichlorophenyl)-2-fluoro-2-(1H-1,2,4-triazol-1-yl)ethan-1-ol;
1-(3-methoxyphenyl)-2-fluoro-2-(1H-1,2,4-triazol-1-yl)ethan-1-ol;
1-(2-methoxyphenyl)-2-fluoro-2-(1H-1,2,4-triazol-1-yl)ethan-1-ol;
1-[4-(4-chlorophenoxy)phenyl]-2-fluoro-2-(1H-1,2,4-triazol-1-yl)ethan-]-ol;
1-[4-(4-chlorophenoxy)phenyl]-2-fluoro-2-(1H-1,2,4-triazol-1-yl)propan-1-ol;
1-[4-(2,4-dichlorophenoxy)phenyl]-2-fluoro-2-(1H-1,2,4-triazol-1-yl)ethan-1-ol;
1-[4-(2,4-dichlorophenoxy)phenyl]-2-fluoro-2-(1H-1,2,4-triazol-1-yl)propan-1-ol;
1-[4-(4-chlorophenoxy)-2-methylphenyl]-2-fluoro-2-(1H-1,2,4-triazol-1-yl)ethan-1-ol.

8. A compound of the formula

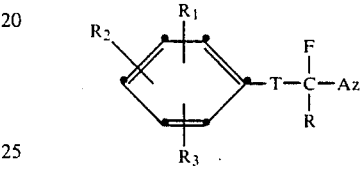

wherein
Az is 1H-1,2,4-triazol-1-yl, 4H-1,2,4-triazol-4-yl or 1H-imidazol-1-yl;

T is —C(O)—, —CH(OH)— or one of the groups

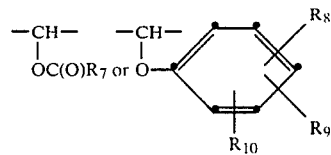

wherein
$R_7$ is $C_1$–$C_6$alkyl which is unsubstituted or substituted by $C_1$–$C_3$-alkoxy, halogen, or cyano, or is $C_3$–$C_6$alkenyl, $C_3$–$C_6$alkynyl, $C_3$–$C_6$cycloalkyl, 2-furyl, 2-tetrahdrofuryl, or is phenyl or benzyl, each unsubstituted or substituted by halogen, nitro, $C_1$–$C_3$alkyl, $C_1$–$C_3$alkoxy, $C_1$–$C_3$haloalkyl or $C_1$–$C_3$haloalkoxy;

$R_8$, $R_9$ and $R_{10}$ are each independently hydrogen, nitro, halogen, cyano, $C_1$–$C_3$alkyl, $C_1$–$C_3$alkoxy, $C_1$–$C_3$haloalkoxy, —COO($C_1$–$C_3$ alkyl), $NH_2$ or $NHCOCH_3$;

R is hydrogen or $C_1$–$C_6$alkyl, provided that if T is —C(O)—, R is $C_1$–$C_6$alkyl;

$R_1$ and $R_2$ are each independently hydrogen, halogen, $C_1$–$C_6$alkyl, $C_1$–$C_6$alkoxy, $C_1$–$C_6$haloalkyl, $C_1$–$C_6$haloalkoxy, nitro or cyano; and $R_3$ is hydrogen, halogen, $C_1$–$C_6$alkyl, $C_1$–$C_6$alkoxy, $C_1$–$C_6$haloalkyl, $C_1$–$C_6$haloalkoxy, nitro, cyano or the group

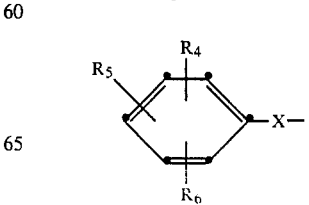

wherein
X is O, S, SO or SO$_2$;
R$_4$, R$_5$ and R$_6$ are each independently hydrogen, halogen, cyano, nitro, C$_1$–C$_6$alkyl, C$_1$–C$_6$alkoxy, C$_1$–C$_6$haloalkyl or C$_1$–C$_6$haloalkoxy; or an acid addition salt or metal complex thereof.

9. A compound according to claim 8 wherein:
T is —C(O)—;
R is C$_1$–C$_6$ alkyl;
R$_1$ and R$_2$ are each independently hydrogen, halogen, C$_1$–C$_6$alkyl, C$_1$–C$_6$alkoxy, C$_1$–C$_6$haloalkyl, C$_1$–C$_6$haloalkoxy, nitro or cyano; and
R$_3$ is hydrogen, halogen, C$_1$–C$_6$alkyl, C$_1$–C$_6$alkoxy, C$_1$–C$_6$haloalkyl, C$_1$–C$_6$haloalkoxy, nitro, cyano or the group

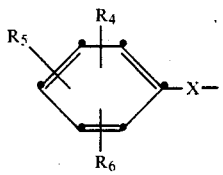

wherein
X is O, S, SO, or SO$_2$;
R$_4$, R$_5$ and R$_6$ are each independently hydrogen, halogen, cyano, nitro, C$_1$–C$_6$alkyl, C$_1$–C$_6$alkoxy, C$_1$–C$_6$haloalkyl or C$_1$–C$_6$haloalkoxy; or an acid addition salt or metal complex thereof.

10. A compound according to claim 9 wherein
Ax is 1H-1,2,4-triazol-1-yl;
R is C$_1$–C$_4$alkyl;
R$_1$ is in the ortho-position and R$_2$ is in the para position and each independently is fluorine, chlorine, bromine, methyl, methoxy, CF$_3$, OCHF$_2$, OCF$_3$, nitro or cyano; and R$_3$ is hydrogen;
or an acid addition salt or metal complex thereof.

11. A compound according to claim 9 wherein:
Az is 1H-1,2,4-triazol-1-yl;
R is C$_1$–C$_4$alkyl;
R$_3$ is the group

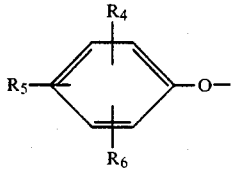

wherein R$_1$, R$_2$, R$_4$, R$_5$ and R$_6$ are each independently hydrogen, fluorine, chlorine, bromine, methyl, methoxy, CF$_3$, OCF$_3$, OCHF$_2$, cyano or nitro.

12. A compound according to claim 13 selected from the group consisting of:
1-(2,4-dichlorophenyl)-2-fluoro-2-(1H-1,2,4-triazol-1-yl)propan-1-one;
1-(2,4-dichlorophenyl)-2-fluoro-2-(1H-imidazol-1-yl)propan-1-one;
1-(2,4-dichlorophenyl)-2-fluoro-2-(1H-1,2,4-triazol-1-yl)butan-1-one;
1-(phenyl)-2-fluoro-2-(1H-1,2,4-triazol-1-yl)propan-1-one;
1-(1-phenyl)-2-fluoro-2-(1H-1,2,4-triazol-1-yl)hexan-1-one;
1-(2,4-dichlorophenyl)-2-fluoro-2-(1H-1,2,4-triazol-1-yl)pentan-1-one;
1-(4-fluorophenyl)-2-fluoro-2-(1H-1,2,4-triazol-1-yl)hexan-1-one;
1-[4-(4-chlorophenoxy)phenyl]-2-fluoro-2-(1H-1,2,4-triazol-1-yl)propan-1-one;
1-[4-(2,4-dichlorophenoxy)phenyl]-2-fluoro-2-(1H-1,2,4-triazol-1-yl)propan-1-one.

13. A composition for controlling phytopathogenic microorganisms or preventing attack by such microorganisms, which composition contains a microbicidally effective amount of at least one compound according to claim 1.

14. A method of controlling phytopathogenic microorganisms or of protecting cultivated plants from attack by such microorganisms, which method comprises applying to said plants or to the locus thereof a microbicidally effective amount of a compound according to claim 1.

15. A method of protecting cultivated rice plants from attack by phytopathogenic microorganisms, which method comprises applying to said plants or to the locus thereof a microbicidally effective amount of a compound according to claim 1.

16. A method of controlling phytopathogenic microorganisms or of protecting cultivated plants from attack by such microorganisms, which method comprises applying to said plants or to the locus thereof a microbicidally effective amount of a compound of the formula

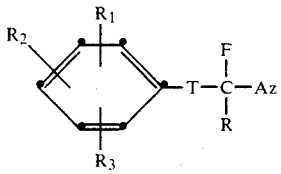

wherein
Az is 1H-1,2,4-triazol-1-yl, 4H-1,2,4-triazol-4-yl or 1H-imidazol-1-yl;
T is —C(O)—, —CH(OH)— or one of the groups

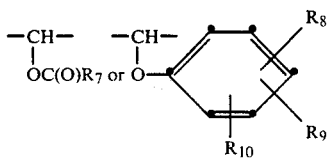

wherein
R$_7$ is C$_1$–C$_6$alkyl which is unsubstituted or substituted by C$_1$–C$_3$-alkoxy, halogen, or cyano, or is C$_3$–C$_6$alkenyl, C$_3$–C$_6$alkynyl, C$_3$–C$_6$cycloalkyl, 2-furyl, 2-tetrahydrofuryl, or is phenyl or benzyl, each unsubstituted or substituted by halogen, nitro, C$_1$–C$_3$alkyl, C$_1$–C$_3$alkoxy, C$_1$–C$_3$haloalkyl or C$_1$–C$_3$haloalkoxy;
R$_8$, R$_9$ and R$_{10}$ are each independently hydrogen, nitro, halogen, cyano, C$_1$–C$_3$alkyl, C$_1$–C$_3$alkoxy, C$_1$–C$_3$haloalkoxy, —COO(C$_1$–C$_3$alkyl), NH$_2$ or NHCOCH$_3$;
R is hydrogen or C$_1$–C$_6$ alkyl;
R$_1$ and R$_2$ are each independently hydrogen, halogen, C$_1$–C$_6$alkyl, C$_1$–C$_6$alkoxy, C$_1$–C$_6$haloalkyl, C$_1$–C$_6$haloalkoxy, nitro or cyano; and $R_3$ is hydrogen, halogen, $C_1$–$C_6$alkyl, $C_1$–$C_6$alkoxy, $C_1$–$C_6$haloalkyl, $C_1$–$C_6$haloalkoxy, nitro, cyano or the group

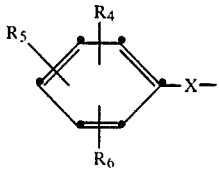

wherein

X is O, S, SO or $SO_2$;

$R_4$, $R_5$ and $R_6$ are each independently hydrogen, halogen, cyano, nitro, $C_1$–$C_6$alkyl, $C_1$–$C_6$alkoxy, $C_1$–$C_6$haloalkyl or $C_1$–$C_6$haloalkoxy; or an acid addition salt or metal complex thereof.

17. A method according to claim 16 wherein said cultivated plants are rice plants.

18. A method according to claim 17 wherein said compound is selected from the group consisting of:
1-(2,4-dichlorophenyl)-2-fluoro-2-(1H-1,2,4-triazol-1-yl)ethan-1-one;
1-(2,4-dichlorophenyl)-2-fluoro-2-(1H-imidazol-1-yl)ethan-1-one;
1-(phenyl)-2-fluoro-2-(1H-1,2,4-triazol-1-yl)ethan-1-one;
1-(4-chlorophenyl)-2-fluoro-2-(1H-1,2,4-triazol-1-yl)ethan-1-one;
1-(3,4-dichlorophenyl)-2-fluoro-2-(1H-1,2,4-triazol-1-yl)ethan-1-one;
1-(2,5-dichlorophenyl)-2-fluoro-2-(1H-1,2,4-triazol-1-yl)ethan-1-one;
1-(2,4-dimethylphenyl)-2-fluoro-2-(1H-1,2,4-triazol-1-yl)ethan-1-one;
1-(4-bromophenyl)-2-fluoro-2-(1H-1,2,4-triazol-1-yl)ethan-1-one;
1-(2,4-difluorophenyl)-2-fluoro-2-(1H-1,2,4-triazol-1-yl)ethan-1-one;
1-(2,3,4-trichlorophenyl)-2-fluoro-2-(1H-1,2,4-triazol-1-yl)ethan-1-one;
1-(3-methoxyphenyl)-2-fluoro-2-(1H-1,2,4-triazol-1-yl)ethan-1-one;
1-(2-methoxyphenyl)-2-fluoro-2-(1H-1,2,4-triazol-1-yl)ethan-1-one;
1-[4-(4-chlorophenoxy)phenyl]-2-fluoro-2-(1H-1,2,4-triazol-1-yl)ethan-1-one;
1-[4-(2,4-dichlorophenoxy)phenyl]-2-fluoro-2-(1H-1,2,4-triazol-1-yl)ethan-1-one;
1-(2,4-dichlorophenyl)-2-fluoro-2-(1H-1,2,4-triazol-1-yl)propan-1-one;
1-(2,4-dichlorophenyl)-2-fluoro-2-(1H-imidazol-1-yl)propan-1-one;
1-(2,4-dichlorophenyl)-2-fluoro-2-(1H-1,2,4-triazol-1-yl)butan-1-one;
1-(phenyl)-2-fluoro-2-(1H-1,2,4-triazol-1-yl)propan-1-one;
1-(1-phenyl)-2-fluoro-2-(1H-1,2,4-triazol-1-yl)hexan-1-one;
1-(2,4-dichlorophenyl)-2-fluoro-2-(1H-1,2,4-triazol-1-yl)pentan-1-one;
1-(4-fluorophenyl)-2-fluoro-2-(1H-1,2,4-triazol-1-yl)hexan-1-one;
1-[4-(4-chlorophenoxy)phenyl]-2-fluoro-2-(1H-1,2,4-triazol-1-yl)propan-1-one;
1-[4-(2,4-dichlorophenoxy)phenyl]-2-fluoro-2-(1H-1,2,4-triazol-1-yl)propan-1-one.

19. A method according to claim 16 wherein said plants are rice plants and said compound is 1-(2,4-dichlorophenyl)-2-fluoro-2-(1H-1,2,4-triazol-1-yl)pentan-1-one.

20. A method according to claim 16 wherein said plants are rice plants and said compound is 1-(2,4-dichlorophenyl)-2-fluoro-2-(1H-1,2,4-triazol-1-yl)pentan-1-ol.

* * * * *